US012653909B2

(12) United States Patent
Pechan

(10) Patent No.: US 12,653,909 B2
(45) Date of Patent: Jun. 16, 2026

(54) MODIFIED AAV CAPSIDS AND USES THEREOF

(71) Applicant: Solid Biosciences Inc., Cambridge, MA (US)

(72) Inventor: Peter Pechan, Newton, MA (US)

(73) Assignee: Solid Biosciences Inc., Charlestown, MA (US)

( * ) Notice: Subject to any disclaimer, the term of this patent is extended or adjusted under 35 U.S.C. 154(b) by 407 days.

(21) Appl. No.: 17/767,554

(22) PCT Filed: Oct. 9, 2020

(86) PCT No.: PCT/US2020/054990
§ 371 (c)(1),
(2) Date: Apr. 8, 2022

(87) PCT Pub. No.: WO2021/072197
PCT Pub. Date: Apr. 15, 2021

(65) Prior Publication Data
US 2024/0261437 A1 Aug. 8, 2024

Related U.S. Application Data

(60) Provisional application No. 63/021,712, filed on May 8, 2020, provisional application No. 62/913,223, filed on Oct. 10, 2019.

(51) Int. Cl.
*A61K 48/00* (2006.01)
*A61P 21/00* (2006.01)
*C07K 14/005* (2006.01)
*C07K 14/47* (2006.01)
*C12N 15/86* (2006.01)

(52) U.S. Cl.
CPC .......... *A61K 48/0058* (2013.01); *A61P 21/00* (2018.01); *C07K 14/005* (2013.01); *C07K 14/4707* (2013.01); *C12N 15/86* (2013.01); *C12N 2750/14122* (2013.01); *C12N 2750/14143* (2013.01); *C12N 2750/14152* (2013.01); *C12N 2830/008* (2013.01)

(58) Field of Classification Search
CPC . A61K 48/0058; A61P 21/00; C07K 14/4707; C12N 15/86
See application file for complete search history.

(56) References Cited

U.S. PATENT DOCUMENTS

| | | |
|---|---|---|
| 6,869,777 B2 | 3/2005 | Chamberlain et al. |
| 7,001,761 B2 | 2/2006 | Xiao |
| 7,510,867 B2 | 3/2009 | Xiao |
| 7,892,824 B2 | 2/2011 | Duan et al. |
| 7,906,111 B2 | 3/2011 | Wilson et al. |
| 8,501,920 B2 | 8/2013 | Chamberlain et al. |
| 10,166,272 B2 | 1/2019 | Dickson et al. |
| 2010/0254896 A1 | 10/2010 | Pasqualini et al. |

| | | | |
|---|---|---|---|
| 2014/0234255 A1* | 8/2014 | Lai | C07K 14/4708 |
| | | | 435/320.1 |
| 2017/0096683 A1 | 4/2017 | Scaria et al. | |
| 2017/0191079 A1 | 7/2017 | Vandenberghe et al. | |

FOREIGN PATENT DOCUMENTS

| | | | |
|---|---|---|---|
| CN | 114207120 A | 3/2022 | |
| JP | 2021-521833 A | 8/2021 | |
| WO | 2015/121501 A1 | 8/2015 | |
| WO | 2015/168666 A2 | 11/2015 | |
| WO | WO-2016055437 A1 * | 4/2016 | ........... A61K 31/573 |
| WO | 2016/115543 A2 | 7/2016 | |
| WO | 2018/129203 A2 | 7/2018 | |
| WO | 2018/189244 A1 | 10/2018 | |
| WO | 2019/207132 A1 | 10/2019 | |
| WO | 2021/072197 A1 | 4/2021 | |

OTHER PUBLICATIONS

Schneider et al., SGT-001 Microdystrophin Gene Therapy for Duchenne Muscular Dystrophy. 2017. Solid Biosciences (Year: 2017).*
Weinmann et al. GenBank ID: QEU45513.1, published Sep. 30, 2019 (Year: 2019).*
Buning et al., Capsid Modifications for Targeting and Improving the Efficacy of AAV Vectors. Mol Ther Methods Clin Dev. Jan. 26, 2019;12:248-265.
Kohlschutter et al., Novel cytotoxic vectors based on adeno-associated virus. Toxins (Basel). Dec. 2010;2(12):2754-68.
International Search Report and Written Opinion for Application No. PCT/US2020/054990, dated Mar. 9, 2021, 11 pages.
Adachi et al., Creation of Liver-Detargeting AAV2-Derived Mutants Based on the Knowledge of AAV9 Capsid Functions. Molecular Therapy. May 2013;21(Suppl 1):Abstract 124, S51.
Andari, Identification of new muscle-tropic Adeno-associated virus (AAV) capsids of treatment of rare hereditary muscular disorders. <www.myocure.eu.> Poster ID 484, 14 pages, Oct. 17, 2018.
Aumailley et al., Identification of the Arg-Gly-Asp sequence in laminin A chain as a latent cell-binding site being exposed in fragment P1. FEBS Lett. Mar. 12, 1990;262(1):82-6.
Deverman et al., Cre-dependent selection yields AAV variants for widespread gene transfer to the adult brain. Nat Biotechnol. Feb. 2016;34(2):204-9.
Gao et al., Clades of Adeno-associated viruses are widely disseminated in human tissues. J Virol. Jun. 2004;78(12):6381-8.

(Continued)

*Primary Examiner* — Arthur S Leonard
*Assistant Examiner* — Nicholas A Humphries
(74) *Attorney, Agent, or Firm* — McCarter & English, LLP; Yu Lu

(57) ABSTRACT

The invention described herein provide a modified VPI capsid enabling preferential targeted expression of gene of interest (GOI) in muscle tissues, as well as recombinant adeno-associated virus (rAAV) with the GOI packaged with the modified VPI capsids, and uses thereof.

21 Claims, 18 Drawing Sheets

Specification includes a Sequence Listing.

(56)                    References Cited

OTHER PUBLICATIONS

Green et al., Characterization of Novel AAV Vectors Engineered for Muscle Gene Delivery. 1 page, Solid Biosciences. 23rd ASGCT Annual Meeting, May 12-15, 2020.

Griffin et al., Adeno-associated Virus Serotype rh74 Prevalence in Muscular Dystrophy Population. American Society of Gene and Cell Therapy (ASGCT) 22nd Annual Meeting. 1 page, Abstract 724, Apr. 29-May 2, 2019.

Johnson et al., Novel adeno-associated virus vector vaccine restricts replication of simian immunodeficiency virus in macaques. J Virol. Jan. 2005;79(2):955-65.

Khabou et al., Insight into the mechanisms of enhanced retinal transduction by the engineered AAV2 capsid variant-7m8. Biotechnol Bioeng. Dec. 2016;113(12):2712-2724.

Kunze et al., Synthetic AAV/CRISPR vectors for blocking HIV-1 expression in persistently infected astrocytes. Glia. Feb. 2018;66(2):413-427.

Michelfelder et al., Successful expansion but not complete restriction of tropism of adeno-associated virus by in vivo biopanning of random virus display peptide libraries. PLoS One. 2009;4(4):e5122, 13 pages.

Michelfelder et al., Vectors selected from adeno-associated viral display peptide libraries for leukemia cell- targeted cytotoxic gene therapy. Exp Hematol. Dec. 2007;35(12):1766-76.

Mietzsch et al., Comparative Analysis of the Capsid Structures of AAVrh.10, AAVrh.39, and AAV8. J Virol. Feb. 28, 2020;94(6):e01769-19.

Nicklin et al., Efficient and selective AAV2-mediated gene transfer directed to human vascular endothelial cells. Mol Ther. Sep. 2001;4(3):174-81.

Pechan et al., Evaluation of a Novel AAV Vector for Muscle Gene Delivery. Solid Biosciences. Poster Presentation. ESGCT/SETGYC Collaborative Congress Barcelona (Spain), Oct. 22-25, 2019.

Perabo et al., In vitro selection of viral vectors with modified tropism: the adeno-associated virus display. Mol Ther. Jul. 2003;8(1):151-7.

Sacher et al., Peptide-Mediated Retargeting of 12 AAV Serotypes. Molecular Therapy. May 2013;21(Suppl 1): Abstract 123, S51.

Varadi et al., Novel random peptide libraries displayed on AAV serotype 9 for selection of endothelial cell-directed gene transfer vectors. Gene Ther. Aug. 2012;19(8):800-9.

Zhang et al., Improvements and Applications of Adeno-associated Virus for Gene Therapy. Journal of Capital Medical University. Aug. 2009;30(4):565-573.

Crudele et al., AAV-based gene therapies for the muscular dystrophies. Hum Mol Genet. Oct. 1, 2019;28(R1):R102-R107.

Gong et al., Adenoassociated virus serotype 9-mediated gene therapy for x-linked adrenoleukodystrophy. Mol Ther. May 2015;23(5):824-834.

Strobel et al., Increasing AAV Vector Yield By Riboswitch-Mediated Attenuation of Toxic Transgene Effects in HEK-293 Producer Cells. Molecular Therapy. May 2015;23:S269-S270, Abstract 678.

Adachi et al., Creation of Liver-Detargeting AAV2-Derived Mutants Based on the Knowledge of AAV9 Capsid Functions. Molecular Therapy. May 2013;21(Suppl 1):S51, Abstract 124.

Girod et al., Genetic capsid modifications allow efficient re-targeting of adeno-associated virus type 2. Nat Med. Sep. 1999;5(9):1052-6.

Michelfelder et al., Peptide ligands incorporated into the threefold spike capsid domain to re-direct gene transduction of AAV8 and AAV9 in vivo. PLoS One. 2011;6(8):e23101, 11 pages.

Rabinowitz et al., Building a better vector: the manipulation of AAV virions. Virology. Dec. 20, 2000;278(2):301-8.

Ried et al., Adeno-associated virus capsids displaying immunoglobulin-binding domains permit antibody-mediated vector retargeting to specific cell surface receptors. J Virol. May 2002;76(9):4559-66.

Tang et al., AAV-directed muscular dystrophy gene therapy. Expert Opin Biol Ther. Mar. 2010;10(3):395-408.

Weinmann et al., Identification of a myotropic AAV by massively parallel in vivo evaluation of barcoded capsid variants. Nat Commun. Oct. 28, 2020;11(1):5432, Supplemental Information, 39 pages.

* cited by examiner

Microdystrophin expression in C2C12 cells

| | Fold Change |
|---|---|
| AAV9 | 1.00 |
| AAV-SLB101 | 10.91 |
| AAV8 | 0.77 |

Microdystrophin expression in DMD patient-derived muscle cells

|  | Fold Change |
|---|---|
| AAV9 | 1.00 |
| AAV-SLB101 | 4.01 |
| AAV8 | 1.45 |

Microdystrophin expression in differentiated C2C12 cells

Microdystrophin expression in differentiated C2C12 cells (normalized to AAV9 @ same MOI)

Microdystrophin expression in differentiated DMD Mouly cells
(outliers removed)

Differentiated DMD Mouly cell transduction by AAV
(normalized to AAV9 @ same MOI)

Production Yield

Uptake into C2C12 cells

| | Fold Change |
|---|---|
| AAV9 | 1.00 |
| AAV-SLB101 | 8.87 |
| AAV-SLB102 | 7.11 |
| AAV-SLB103 | 1.19 |
| AAV-SLB104 | 0.87 |
| AAV-SLB105 | 1.51 |
| AAV-SLB106 | 1.51 |
| AAV-SLB107 | 1.72 |
| AAV-SLB108 | 1.24 |
| AAV-SLB109 | 1.91 |
| AAV-SLB110 | 0.90 |
| AAV-SLB111 | 7.72 |
| AAV-SLB112 | 4.92 |
| AAV-SLB113 | 4.11 |
| AAV-SLB114 | 1.94 |

FIG. 6

| | | | |
|---|---|---|---|
| AAV9: | NHQ SAQ | | AQAQ TGW |
| SLB101: | NHQ SAQ | RGDLGLS | AQAQ TGW |
| SLB113: | NHQ SGQA | GRGDLGLS | AQAA TGW |
| SLB114: | NHQ GQS | GRGDLGLS | AQAAQ TGW |

SEQUENCE LISTING

```
<160> NUMBER OF SEQ ID NOS: 38

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Gly Asp Leu Gly Leu Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Gly Asp Met Ser Arg Glu
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Glu Ala Arg Ile Ser Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Ser Gly Leu Ser Gln Ser
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Tyr Arg Asp Ser Ser Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Leu Gly Ser Ala Arg Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Gly Asn Ser Gly Ala Ala
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Asp Cys Arg Gly Asp Cys Phe Cys
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Asp Val Arg Ser Ala Asn
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

-continued

```
Asn Asp Val Arg Ala Val Ser
1               5

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Arg Gly Asp Leu Gly Leu Ser Gly Gly Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Ser Arg Gly Asp Leu Gly Leu Ser Gly Gly Ser
1               5                   10

<210> SEQ ID NO 13
<211> LENGTH: 736
<212> TYPE: PRT
<213> ORGANISM: Adeno-associated virus

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205
```

-continued

```
Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
```

-continued

```
625                    630                    635                    640

Lys His Pro Pro Pro Gln Ile Leu Ile Lys Asn Thr Pro Val Pro Ala
                  645                    650                    655

Asp Pro Pro Thr Ala Phe Asn Lys Asp Lys Leu Asn Ser Phe Ile Thr
                  660                    665                    670

Gln Tyr Ser Thr Gly Gln Val Ser Val Glu Ile Glu Trp Glu Leu Gln
                  675                    680                    685

Lys Glu Asn Ser Lys Arg Trp Asn Pro Glu Ile Gln Tyr Thr Ser Asn
         690                    695                    700

Tyr Tyr Lys Ser Asn Asn Val Glu Phe Ala Val Asn Thr Glu Gly Val
705                    710                    715                    720

Tyr Ser Glu Pro Arg Pro Ile Gly Thr Arg Tyr Leu Thr Arg Asn Leu
                  725                    730                    735
```

<210> SEQ ID NO 14
<211> LENGTH: 743
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Met Ala Ala Asp Gly Tyr Leu Pro Asp Trp Leu Glu Asp Asn Leu Ser
1               5                    10                    15

Glu Gly Ile Arg Glu Trp Trp Ala Leu Lys Pro Gly Ala Pro Gln Pro
                  20                    25                    30

Lys Ala Asn Gln Gln His Gln Asp Asn Ala Arg Gly Leu Val Leu Pro
         35                    40                    45

Gly Tyr Lys Tyr Leu Gly Pro Gly Asn Gly Leu Asp Lys Gly Glu Pro
         50                    55                    60

Val Asn Ala Ala Asp Ala Ala Ala Leu Glu His Asp Lys Ala Tyr Asp
65                    70                    75                    80

Gln Gln Leu Lys Ala Gly Asp Asn Pro Tyr Leu Lys Tyr Asn His Ala
                  85                    90                    95

Asp Ala Glu Phe Gln Glu Arg Leu Lys Glu Asp Thr Ser Phe Gly Gly
                  100                   105                   110

Asn Leu Gly Arg Ala Val Phe Gln Ala Lys Lys Arg Leu Leu Glu Pro
         115                   120                   125

Leu Gly Leu Val Glu Glu Ala Ala Lys Thr Ala Pro Gly Lys Lys Arg
         130                   135                   140

Pro Val Glu Gln Ser Pro Gln Glu Pro Asp Ser Ser Ala Gly Ile Gly
145                   150                   155                   160

Lys Ser Gly Ala Gln Pro Ala Lys Lys Arg Leu Asn Phe Gly Gln Thr
                  165                   170                   175

Gly Asp Thr Glu Ser Val Pro Asp Pro Gln Pro Ile Gly Glu Pro Pro
                  180                   185                   190

Ala Ala Pro Ser Gly Val Gly Ser Leu Thr Met Ala Ser Gly Gly Gly
         195                   200                   205

Ala Pro Val Ala Asp Asn Asn Glu Gly Ala Asp Gly Val Gly Ser Ser
         210                   215                   220

Ser Gly Asn Trp His Cys Asp Ser Gln Trp Leu Gly Asp Arg Val Ile
225                   230                   235                   240

Thr Thr Ser Thr Arg Thr Trp Ala Leu Pro Thr Tyr Asn Asn His Leu
                  245                   250                   255
```

-continued

```
Tyr Lys Gln Ile Ser Asn Ser Thr Ser Gly Gly Ser Ser Asn Asp Asn
            260             265             270

Ala Tyr Phe Gly Tyr Ser Thr Pro Trp Gly Tyr Phe Asp Phe Asn Arg
        275             280             285

Phe His Cys His Phe Ser Pro Arg Asp Trp Gln Arg Leu Ile Asn Asn
        290             295             300

Asn Trp Gly Phe Arg Pro Lys Arg Leu Asn Phe Lys Leu Phe Asn Ile
305             310             315             320

Gln Val Lys Glu Val Thr Asp Asn Asn Gly Val Lys Thr Ile Ala Asn
            325             330             335

Asn Leu Thr Ser Thr Val Gln Val Phe Thr Asp Ser Asp Tyr Gln Leu
            340             345             350

Pro Tyr Val Leu Gly Ser Ala His Glu Gly Cys Leu Pro Pro Phe Pro
            355             360             365

Ala Asp Val Phe Met Ile Pro Gln Tyr Gly Tyr Leu Thr Leu Asn Asp
        370             375             380

Gly Ser Gln Ala Val Gly Arg Ser Ser Phe Tyr Cys Leu Glu Tyr Phe
385             390             395             400

Pro Ser Gln Met Leu Arg Thr Gly Asn Asn Phe Gln Phe Ser Tyr Glu
            405             410             415

Phe Glu Asn Val Pro Phe His Ser Ser Tyr Ala His Ser Gln Ser Leu
            420             425             430

Asp Arg Leu Met Asn Pro Leu Ile Asp Gln Tyr Leu Tyr Tyr Leu Ser
            435             440             445

Lys Thr Ile Asn Gly Ser Gly Gln Asn Gln Gln Thr Leu Lys Phe Ser
        450             455             460

Val Ala Gly Pro Ser Asn Met Ala Val Gln Gly Arg Asn Tyr Ile Pro
465             470             475             480

Gly Pro Ser Tyr Arg Gln Gln Arg Val Ser Thr Thr Val Thr Gln Asn
            485             490             495

Asn Asn Ser Glu Phe Ala Trp Pro Gly Ala Ser Ser Trp Ala Leu Asn
            500             505             510

Gly Arg Asn Ser Leu Met Asn Pro Gly Pro Ala Met Ala Ser His Lys
            515             520             525

Glu Gly Glu Asp Arg Phe Phe Pro Leu Ser Gly Ser Leu Ile Phe Gly
        530             535             540

Lys Gln Gly Thr Gly Arg Asp Asn Val Asp Ala Asp Lys Val Met Ile
545             550             555             560

Thr Asn Glu Glu Glu Ile Lys Thr Thr Asn Pro Val Ala Thr Glu Ser
            565             570             575

Tyr Gly Gln Val Ala Thr Asn His Gln Ser Ala Gln Arg Gly Asp Leu
            580             585             590

Gly Leu Ser Ala Gln Ala Gln Thr Gly Trp Val Gln Asn Gln Gly Ile
        595             600             605

Leu Pro Gly Met Val Trp Gln Asp Arg Asp Val Tyr Leu Gln Gly Pro
        610             615             620

Ile Trp Ala Lys Ile Pro His Thr Asp Gly Asn Phe His Pro Ser Pro
625             630             635             640

Leu Met Gly Gly Phe Gly Met Lys His Pro Pro Pro Gln Ile Leu Ile
            645             650             655

Lys Asn Thr Pro Val Pro Ala Asp Pro Pro Thr Ala Phe Asn Lys Asp
            660             665             670

Lys Leu Asn Ser Phe Ile Thr Gln Tyr Ser Thr Gly Gln Val Ser Val
```

-continued

```
                  675                 680                 685

Glu Ile Glu Trp Glu Leu Gln Lys Glu Asn Ser Lys Arg Trp Asn Pro
    690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740

<210> SEQ ID NO 15
<211> LENGTH: 749
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala Ala Asp Gly Tyr Leu Pro Asp Trp Leu Glu Asp Asn Leu Ser
1                   5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Gly Gly Gly Arg
                580                 585                 590

Gly Asp Leu Gly Leu Ser Gly Gly Ala Gln Ala Gln Thr Gly Trp
                595                 600                 605

Val Gln Asn Gln Gly Ile Leu Pro Gly Met Val Trp Gln Asp Arg Asp
    610                 615                 620

Val Tyr Leu Gln Gly Pro Ile Trp Ala Lys Ile Pro His Thr Asp Gly
625                 630                 635                 640

Asn Phe His Pro Ser Pro Leu Met Gly Gly Phe Gly Met Lys His Pro
                645                 650                 655

Pro Pro Gln Ile Leu Ile Lys Asn Thr Pro Val Pro Ala Asp Pro Pro
                660                 665                 670

Thr Ala Phe Asn Lys Asp Lys Leu Asn Ser Phe Ile Thr Gln Tyr Ser
                675                 680                 685

Thr Gly Gln Val Ser Val Glu Ile Glu Trp Glu Leu Gln Lys Glu Asn
    690                 695                 700

Ser Lys Arg Trp Asn Pro Glu Ile Gln Tyr Thr Ser Asn Tyr Tyr Lys
```

-continued

```
705                 710                 715                 720
Ser Asn Asn Val Glu Phe Ala Val Asn Thr Glu Gly Val Tyr Ser Glu
                725                 730                 735

Pro Arg Pro Ile Gly Thr Arg Tyr Leu Thr Arg Asn Leu
            740                 745

<210> SEQ ID NO 16
<211> LENGTH: 749
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320
```

-continued

```
Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Gly Gly Ser Arg
            580                 585                 590

Gly Asp Leu Gly Leu Ser Gly Gly Ser Ala Gln Ala Gln Thr Gly Trp
            595                 600                 605

Val Gln Asn Gln Gly Ile Leu Pro Gly Met Val Trp Gln Asp Arg Asp
        610                 615                 620

Val Tyr Leu Gln Gly Pro Ile Trp Ala Lys Ile Pro His Thr Asp Gly
625                 630                 635                 640

Asn Phe His Pro Ser Pro Leu Met Gly Gly Phe Gly Met Lys His Pro
                645                 650                 655

Pro Pro Gln Ile Leu Ile Lys Asn Thr Pro Val Pro Ala Asp Pro Pro
            660                 665                 670

Thr Ala Phe Asn Lys Asp Lys Leu Asn Ser Phe Ile Thr Gln Tyr Ser
            675                 680                 685

Thr Gly Gln Val Ser Val Glu Ile Glu Trp Glu Leu Gln Lys Glu Asn
        690                 695                 700

Ser Lys Arg Trp Asn Pro Glu Ile Gln Tyr Thr Ser Asn Tyr Tyr Lys
705                 710                 715                 720

Ser Asn Asn Val Glu Phe Ala Val Asn Thr Glu Gly Val Tyr Ser Glu
                725                 730                 735

Pro Arg Pro Ile Gly Thr Arg Tyr Leu Thr Arg Asn Leu
```

-continued

```
                  740                   745

<210> SEQ ID NO 17
<211> LENGTH: 13
<212> TYPE: PRT
<213> ORGANISM: Adeno-associated virus

<400> SEQUENCE: 17

Asn His Gln Ser Ala Gln Ala Gln Ala Gln Thr Gly Trp
1               5                   10

<210> SEQ ID NO 18
<211> LENGTH: 13
<212> TYPE: PRT
<213> ORGANISM: Adeno-associated virus

<400> SEQUENCE: 18

Asn Leu Gln Gln Gln Asn Thr Ala Pro Gln Ile Gly Thr
1               5                   10

<210> SEQ ID NO 19
<211> LENGTH: 13
<212> TYPE: PRT
<213> ORGANISM: Adeno-associated virus

<400> SEQUENCE: 19

Asn Leu Gln Gln Gln Asn Ala Ala Pro Ile Val Gly Ala
1               5                   10

<210> SEQ ID NO 20
<211> LENGTH: 13
<212> TYPE: PRT
<213> ORGANISM: Adeno-associated virus

<400> SEQUENCE: 20

Asn Leu Gln Gln Gln Asn Thr Gly Pro Ile Val Gly Asn
1               5                   10

<210> SEQ ID NO 21
<211> LENGTH: 13
<212> TYPE: PRT
<213> ORGANISM: Adeno-associated virus

<400> SEQUENCE: 21

Asn Leu Gln Ser Ser Ser Thr Asp Pro Ala Thr Gly Asp
1               5                   10

<210> SEQ ID NO 22
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: R, G, E, D, S, C, N, or absent
<220> FEATURE:
<221> NAME/KEY: MOD_RES
<222> LOCATION: (30)..(30)
<223> OTHER INFORMATION: G, E, S, Y, L, D, or absent
<220> FEATURE:
<221> NAME/KEY: MOD_RES
<222> LOCATION: (31)..(31)
<223> OTHER INFORMATION: D, A, G, R, N, C, V, S, or absent
<220> FEATURE:
<221> NAME/KEY: MOD_RES
```

```
<222> LOCATION: (32)..(32)
<223> OTHER INFORMATION: L, M, R, D, S, or absent
<220> FEATURE:
<221> NAME/KEY: MOD_RES
<222> LOCATION: (33)..(33)
<223> OTHER INFORMATION: G, S, I, A, or absent
<220> FEATURE:
<221> NAME/KEY: MOD_RES
<222> LOCATION: (34)..(34)
<223> OTHER INFORMATION: L, R, S, Q, A, D, V, or absent
<220> FEATURE:
<221> NAME/KEY: MOD_RES
<222> LOCATION: (35)..(35)
<223> OTHER INFORMATION: S, E, A, G, C, N, or absent

<400> SEQUENCE: 22

Thr Asn Glu Glu Glu Ile Lys Thr Thr Asn Pro Val Ala Thr Glu Ser
1               5                   10                  15

Tyr Gly Gln Val Ala Thr Asn His Gln Ser Ala Gln Xaa Xaa Xaa Xaa
                20                  25                  30

Xaa Xaa Xaa Ala Gln Ala Gln Thr Gly Trp Val Gln Asn Gln Gly Ile
        35                  40                  45

Leu

<210> SEQ ID NO 23
<211> LENGTH: 42
<212> TYPE: PRT
<213> ORGANISM: Adeno-associated virus

<400> SEQUENCE: 23

Thr Asn Glu Glu Glu Ile Lys Thr Thr Asn Pro Val Ala Thr Glu Ser
1               5                   10                  15

Tyr Gly Gln Val Ala Thr Asn His Gln Ser Ala Gln Ala Gln Ala Gln
                20                  25                  30

Thr Gly Trp Val Gln Asn Gln Gly Ile Leu
        35                  40

<210> SEQ ID NO 24
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Thr Asn Glu Glu Glu Ile Lys Thr Thr Asn Pro Val Ala Thr Glu Ser
1               5                   10                  15

Tyr Gly Gln Val Ala Thr Asn His Gln Ser Ala Gln Arg Gly Asp Leu
                20                  25                  30

Gly Leu Ser Ala Gln Ala Gln Thr Gly Trp Val Gln Asn Gln Gly Ile
        35                  40                  45

Leu

<210> SEQ ID NO 25
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Thr Asn Glu Glu Glu Ile Lys Thr Thr Asn Pro Val Ala Thr Glu Ser
```

-continued

```
1               5                    10                   15

Tyr Gly Gln Val Ala Thr Asn His Gln Ser Ala Gln Arg Gly Asp Met
            20                   25                   30

Ser Arg Glu Ala Gln Ala Gln Thr Gly Trp Val Gln Asn Gln Gly Ile
        35                   40                   45

Leu

<210> SEQ ID NO 26
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Thr Asn Glu Glu Glu Ile Lys Thr Thr Asn Pro Val Ala Thr Glu Ser
1               5                    10                   15

Tyr Gly Gln Val Ala Thr Asn His Gln Ser Ala Gln Gly Glu Ala Arg
            20                   25                   30

Ile Ser Ala Ala Gln Ala Gln Thr Gly Trp Val Gln Asn Gln Gly Ile
        35                   40                   45

Leu

<210> SEQ ID NO 27
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Thr Asn Glu Glu Glu Ile Lys Thr Thr Asn Pro Val Ala Thr Glu Ser
1               5                    10                   15

Tyr Gly Gln Val Ala Thr Asn His Gln Ser Ala Gln Glu Ser Gly Leu
            20                   25                   30

Ser Gln Ser Ala Gln Ala Gln Thr Gly Trp Val Gln Asn Gln Gly Ile
        35                   40                   45

Leu

<210> SEQ ID NO 28
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Thr Asn Glu Glu Glu Ile Lys Thr Thr Asn Pro Val Ala Thr Glu Ser
1               5                    10                   15

Tyr Gly Gln Val Ala Thr Asn His Gln Ser Ala Gln Glu Tyr Arg Asp
            20                   25                   30

Ser Ser Gly Ala Gln Ala Gln Thr Gly Trp Val Gln Asn Gln Gly Ile
        35                   40                   45

Leu

<210> SEQ ID NO 29
<211> LENGTH: 49
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Thr Asn Glu Glu Glu Ile Lys Thr Thr Asn Pro Val Ala Thr Glu Ser
1               5                   10                  15

Tyr Gly Gln Val Ala Thr Asn His Gln Ser Ala Gln Asp Leu Gly Ser
            20                  25                  30

Ala Arg Ala Ala Gln Ala Gln Thr Gly Trp Val Gln Asn Gln Gly Ile
        35                  40                  45

Leu

<210> SEQ ID NO 30
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Thr Asn Glu Glu Glu Ile Lys Thr Thr Asn Pro Val Ala Thr Glu Ser
1               5                   10                  15

Tyr Gly Gln Val Ala Thr Asn His Gln Ser Ala Gln Ser Gly Asn Ser
            20                  25                  30

Gly Ala Ala Ala Gln Ala Gln Thr Gly Trp Val Gln Asn Gln Gly Ile
        35                  40                  45

Leu

<210> SEQ ID NO 31
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Thr Asn Glu Glu Glu Ile Lys Thr Thr Asn Pro Val Ala Thr Glu Ser
1               5                   10                  15

Tyr Gly Gln Val Ala Thr Asn His Gln Ser Ala Gln Cys Asp Cys Arg
            20                  25                  30

Gly Asp Cys Phe Cys Ala Gln Ala Gln Thr Gly Trp Val Gln Asn Gln
        35                  40                  45

Gly Ile Leu
    50

<210> SEQ ID NO 32
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Thr Asn Glu Glu Glu Ile Lys Thr Thr Asn Pro Val Ala Thr Glu Ser
1               5                   10                  15

Tyr Gly Gln Val Ala Thr Asn His Gln Ser Ala Gln Asn Asp Val Arg
```

-continued

```
                20                  25                  30

Ser Ala Asn Ala Gln Ala Gln Thr Gly Trp Val Gln Asn Gln Gly Ile
        35                  40                  45

Leu

<210> SEQ ID NO 33
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Thr Asn Glu Glu Glu Ile Lys Thr Thr Asn Pro Val Ala Thr Glu Ser
1               5                   10                  15

Tyr Gly Gln Val Ala Thr Asn His Gln Ser Ala Gln Asn Asp Val Arg
                20                  25                  30

Ala Val Ser Ala Gln Ala Gln Thr Gly Trp Val Gln Asn Gln Gly Ile
        35                  40                  45

Leu

<210> SEQ ID NO 34
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Thr Asn Glu Glu Glu Ile Lys Thr Thr Asn Pro Val Ala Thr Glu Ser
1               5                   10                  15

Tyr Gly Gln Val Ala Thr Asn His Gln Ser Ala Gln Gly Gly Gly Arg
                20                  25                  30

Gly Asp Leu Gly Leu Ser Gly Gly Gly Ala Gln Ala Gln Thr Gly Trp
        35                  40                  45

Val Gln Asn Gln Gly Ile Leu
    50                  55

<210> SEQ ID NO 35
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Thr Asn Glu Glu Glu Ile Lys Thr Thr Asn Pro Val Ala Thr Glu Ser
1               5                   10                  15

Tyr Gly Gln Val Ala Thr Asn His Gln Ser Ala Gln Gly Gly Ser Arg
                20                  25                  30

Gly Asp Leu Gly Leu Ser Gly Gly Ser Ala Gln Ala Gln Thr Gly Trp
        35                  40                  45

Val Gln Asn Gln Gly Ile Leu
    50                  55

<210> SEQ ID NO 36
<211> LENGTH: 22
<212> TYPE: PRT
```

-continued

```
<213> ORGANISM: Artificial Sequence
<220> FEATURE:
<223> OTHER INFORMATION: Description of Artificial Sequence: Synthetic
      polypeptide

<400> SEQUENCE: 36

Asn His Gln Ser Gly Gln Ala Gly Arg Gly Asp Leu Gly Leu Ser Ala
1               5                   10                  15

Gln Ala Ala Thr Gly Trp
            20

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asn His Gln Gly Gln Ser Gly Arg Gly Asp Leu Gly Leu Ser Ala Gln
1               5                   10                  15

Ala Ala Gln Thr Gly Trp
            20

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asn His Gln Ser Ala Gln Arg Gly Asp Leu Gly Leu Ser Ala Gln Ala
1               5                   10                  15

Gln Thr Gly Trp
            20
```

MODIFIED AAV CAPSIDS AND USES THEREOF

REFERENCE TO RELATED APPLICATIONS

This application is a U.S. national stage application filed under 35 U.S.C. § 371, based on International Patent Application No. PCT/US2020/054990, filed on Oct. 9, 2020, which claims the benefit of the filing dates of U.S. Provisional Patent Application Nos. 62/913,223, filed on Oct. 10, 2019, and 63/021,712, filed on May 8, 2020. The entire contents of each of the foregoing applications are incorporated herein by reference.

REFERENCE TO SEQUENCE LISTING

This application is being filed with a Sequence Listing in electronic format. The Sequence Listing file, named 129159_01603_SL, was created on Jan. 24, 2024, and is 39,313 bytes in size. The information in electronic format of the Sequence Listing is incorporated herein by reference in its entirety.

BACKGROUND OF THE INVENTION

Recombinant adeno-associated viral (rAAV) vectors demonstrate great promise as the leading platform for in vivo gene delivery. A variety of rAAV vectors enable delivery to multiple tissues, including the muscular system, for the treatment of many genetic and other complex diseases. Some natural serotypes as well as engineered rAAV capsids exhibit enhanced widespread biodistribution to muscle, which could reduce the total dose required.

Previously, muscular gene delivery was performed by direct injection of rAAV vectors into muscle. More recently, intravenous (IV) administration of rAAV has been increasingly employed to facilitate distribution to many types of muscle and is now the preferred administration route for several clinical trials.

SUMMARY OF THE INVENTION

One aspect of the invention provides a modified adeno-associate virus (mAAV) capsid polypeptide comprising a polypeptide selected from the group consisting of SEQ ID NOs: 1-12, wherein the polypeptide is inserted between residues 588 and 589 of wild-type AAV9 VPI capsid, or the two corresponding residues of a non-AAV9 wild-type Clad F (e.g., AAVhu.32), a wild-type Clad A (e.g., AAV1/6), or a wild-type Clad E (e.g., AAV8, AAVrh.10, or AAVrh.74) VP1 capsid. That is, other than the polypeptide of any one of SEQ ID NOs: 1-12 inserted between residues 588 and 589 of the wild-type AAV9 VPI capsid, or the two corresponding residues of a non-AAV9 wild-type Clad F (e.g., AAVhu.32), a wild-type Clad A (e.g., AAV6), or a wild-type Clad E (e.g., AAV8, AAVrh.10, or AAVrh.74) VP1 capsid, there is no other sequence changes in the wild-type Clad F (e.g., AAV9 or AAVhu.32), wild-type Clad A (e.g., AAV6), or wild-type Clad E (e.g., AAV8, AAVrh.10, or AAVrh.74) VP1 capsid.

In other words, the invention provides a modified adeno-associate virus (mAAV) capsid polypeptide comprising a polypeptide inserted between residues 588 and 589 of wild-type AAV9 VPI capsid, or the two corresponding residues of a non-AAV9 wild-type Clad F (e.g., AAVhu.32), a wild-type Clad A (e.g., AAV6), or a wild-type Clad E (e.g., AAV8, AAVrh.10, or AAVrh.74) VP1 capsid, wherein said polypeptide inserted between residues 588 and 589 of wild-type AAV9 VPI capsid, or the two corresponding residues of a non-AAV9 wild-type Clad F (e.g., AAVhu.32), a wild-type Clad A (e.g., AAV6), or a wild-type Clad E (e.g., AAV8, AAVrh.10, or AAVrh.74) VP1 capsid, comprises, consists essentially of, or consists of the amino acid sequence of any one of SEQ ID NOs: 1-12.

In certain embodiments, the mAAV capsid polypeptide comprises the polypeptide of SEQ ID NO: 1, 11, or 12.

That is, a specific aspect of the invention provides a modified adeno-associate virus (mAAV) capsid polypeptide comprising, consisting essentially of, or consisting of the polypeptide of SEQ ID NO: 1.

In a related specific aspect, the invention provides a modified adeno-associate virus (mAAV) capsid polypeptide comprising, consisting essentially of, or consisting of the polypeptide of SEQ ID NO: 11.

In yet another specific aspect, the invention provides a modified adeno-associate virus (mAAV) capsid polypeptide comprising, consisting essentially of, or consisting of the polypeptide of SEQ ID NO: 12.

Another aspect of the invention provides a recombinant adeno-associated virus (rAAV, such as a recombinant AAV6, AAV8, AAVrh.74, or AAV9), comprising any one of the subject mAAV capsid polypeptide described herein.

In certain embodiments, the VP1 capsid of the rAAV consists of or consists essentially of any one of the mAAV capsid polypeptide of the invention.

In Certain Embodiments, the rAAV Comprises a Gene of Interest (GOI) Flanked by a Pair of AAV ITR Sequences.

In certain embodiments, the pair of AAV ITR sequences are AAV2, AAV6, AAV8, AAVrh.74, or AAV9 ITR sequences.

In certain embodiments, the gene of interest (GOI) includes a gene responsible for /defective in LGMD2E (limb-girdle muscular dystrophy type 2E), LGMD2D (limb-girdle muscular dystrophy type 2D), LGMD2C (limb-girdle muscular dystrophy type 2C), LGMD2B (limb-girdle muscular dystrophy type 2B), LGMD2L (limb-girdle muscular dystrophy type 2L), LGMD2I (limb-girdle muscular dystrophy type 21), or a gene or coding sequence for NAGLU (α-N-acetylglucosaminidase, for Sanfilippo syndrome or mucopolysaccharidosis type IIIB (MPS IIIB)), sulfamidase or SGSH (for mucopolysaccharidosis type IIIA or MPS IIIA), Factor IX, Factor VIII, Myotubularin 1 (MTM1), Survival of Motor Neuron (SMN, for spinal muscular atrophy or SMA), GalNAc transferase GALGT2, calpain-3 (CAPN-3), acid alpha-glucosidase (GAA, for Pompe disease), alpha-galactosidase A or GLA (for Fabry disease), glucocerebrosidase, dystrophin or microdystrophin.

In certain embodiments, the GOI encodes a microdystrophin.

In certain embodiments, the microdystrophin is one described in U.S. Pat. Nos. 7,906,111; 7,001,761; 7,510,867; 6,869,777; 8,501,920; 7,892,824; PCT/US2016/013733; or U.S. Pat. No. 10,166,272.

In certain embodiments, the microdystrophin comprises a coding sequence for R16 and R17 spectrin-like repeats for the full length dystrophin protein (such as one described in U.S. Pat. No. 7,892,824).

In certain embodiments, the microdystrophin comprises a coding sequence for the R1, R16, R17, R23, and R24 spectrin-like repeats of the full-length dystrophin protein; or a microdystrophin gene described in PCT/US2016/013733 or U.S. Pat. No. 10,479,821.

In certain embodiments, the GOI is operatively linked to a transcriptional regulatory cassette, such as a muscle specific promoter (e.g., a CK8 promoter or a cardiac troponin T (cTnT) promoter).

In certain embodiments, the GOI is a micro-dystrophin gene encoding a protein comprising, from N- to C-terminus, an amino-terminal actin-binding (AB1) domain, a β-dystroglycan binding domain, a Hinge 1 domain (H1), a spectrin-like repeat domain consisting of five spectrin-like repeats that include spectrin-like repeat 1 (SR1), spectrin-like repeat 16 (SR16), spectrin-like repeat 17 (SR17), spectrin-like repeat 23 (SR23), and spectrin-like repeat 24 (SR24), and a Hinge 4 domain (H4), wherein the micro-dystrophin gene is operatively linked to a muscle-specific human muscle creatine kinase CK8 promoter (e.g., SEQ ID NO:19 of U.S. Pat. No. 10,479,821), and wherein the GOI is flanked by a pair of AAV2 ITR (inverted terminal repeat) sequence.

Another aspect of the invention provides a polynucleotide encoding the modified adeno-associate virus (mAAV) capsid polypeptide of the invention, or a polypeptide sequence at least 95%, 96%, 97%, 98%, or 99% identical thereto.

In certain embodiments, the polynucleotide is codon-optimized for mammalian expression.

Another aspect of the invention provides a vector comprising the polynucleotide of the invention.

In certain embodiments, the vector is a plasmid or a viral vector (such as an HSV vector, or an AAV vector).

Another aspect of the invention provides a cultured host cell comprising: (a) a recombinant nucleic acid molecule encoding: (1) the modified adeno-associate virus (mAAV) capsid polypeptide of the invention, or (2) a sequence at least 95%, 96%, 97%, 98%, or 99% identical to (1), wherein the recombinant nucleic acid molecule optionally further comprises a heterologous non-AAV sequence; or, (b) a recombinant adeno-associated virus (rAAV) of the invention.

Another aspect of the invention provides a method of treating a disease or condition such as muscular dystrophy in a subject in need thereof, the method comprises administering to the subject a therapeutically effective amount of any one of the rAAV of the invention.

In certain embodiments, when compared to an otherwise identical reference rAAV with wild-type AAV9 VPI capsid, the GOI of the rAAV is preferentially expressed in cardiac muscle, skeletal muscle, and/or smooth muscle (e.g., smooth muscle in diaphragm).

In certain embodiments, when compared to an otherwise identical reference rAAV with wild-type AAV9 VPI capsid, the GOI of the rAAV is expressed in liver at a statistically significantly lower level.

In certain embodiments, the muscular dystrophy is DMD (Duchenne Muscular Dystrophy) or BMD (Becker Muscular Dystrophy).

In certain embodiments, (1) the muscular dystrophy is LGMD2E (limb-girdle muscular dystrophy type 2E), LGMD2D (limb-girdle muscular dystrophy type 2D), LGMD2C (limb-girdle muscular dystrophy type 2C), LGMD2B (limb-girdle muscular dystrophy type 2B), LGMD2L (limb-girdle muscular dystrophy type 2L), LGMD2I (limb-girdle muscular dystrophy type 21), or spinal muscular atrophy or SMA; (2) the disease or condition is Sanfilippo syndrome or mucopolysaccharidosis type IIIB (MPS IIIB), mucopolysaccharidosis type IIIA or MPS IIIA, Pompe disease, or Fabry disease; or, (3) the disease or condition is characterized or caused by a genetic defect in a gene encoding Factor IX, Factor VIII, Myotubularin 1 (MTM1), GalNAc transferase GALGT2, calpain-3 (CAPN-3), or glucocerebrosidase.

Another aspect of the invention provides a method of producing rAAV, wherein the rAAV comprises any one of the mAAV capsid polypeptide of the invention, the method comprising introducing a rAAV vector encoding a GOI flanked by a pair of ITR sequences to a producing or packaging cell line expressing any one of the mAAV capsid polypeptide of the invention.

In certain embodiments, the producing or packaging cell line is infected by an HSV vector encoding the mAAV capsid polypeptide of the invention.

In certain embodiments, the producing or packaging cell line is transfected by endoing sequence encoding the mAAV capsid polypeptide of the invention.

In certain embodiments, the producing or packaging cell line is HEK293 cells, A549 cells, or HeLa cells.

It should be understood that any one embodiment of the invention, including those described only in the examples or under one aspect of the invention, can be combined with any one or more other embodiment of the invention unless explicitly disclaimed or improper.

BRIEF DESCRIPTION OF THE DRAWINGS

FIG. 5A shows quantification of AAV capsid binding to the cell surface of C2C12 cells as measured by qPCR of DNA isolated after 1 hour of incubation at 4° C. AAV-SLB101 (p<0.0001), -112 (p<0.01) and -114 (p<0.001) bind to C2C12 cells significantly more than AAV9. Statistics are determined by ordinary one-way ANOVA. FIG. 5B shows quantification of uptake of AAV into C2C12 cells as measured by qPCR of DNA isolated after 1 hour of incubation at 4° C. followed by an additional hour at 37° C. AAV-SLB101, 102, 108, 111, 112, 113, 114 were taken up by C2C12 cells significantly more than AAV9 (p<0.0001). Statistics are determined by ordinary one-way ANOVA. In FIG. 5C, C2C12 cells were transduced with microdystrophin-expressing vectors packaged in AAV9, AAV-SLB101 and thirteen additional capsids (AAV-SLB 102 to AAV-SLB114). Cells were harvested 96 hours after transduction and microdystrophin expression was measured. The data shown are normalized to AAV9 and fold change is indicated in the table. AAV-SLB101, 102, 111, 112 and 113 had the highest microdystrophin protein expression over AAV9 (p<0.0001), with AAV-SLB109 and 114 resulting in only slightly higher expression than AAV9 (p<0.001). Statistics are determined by ordinary one-way ANOVA.

Figure 6:
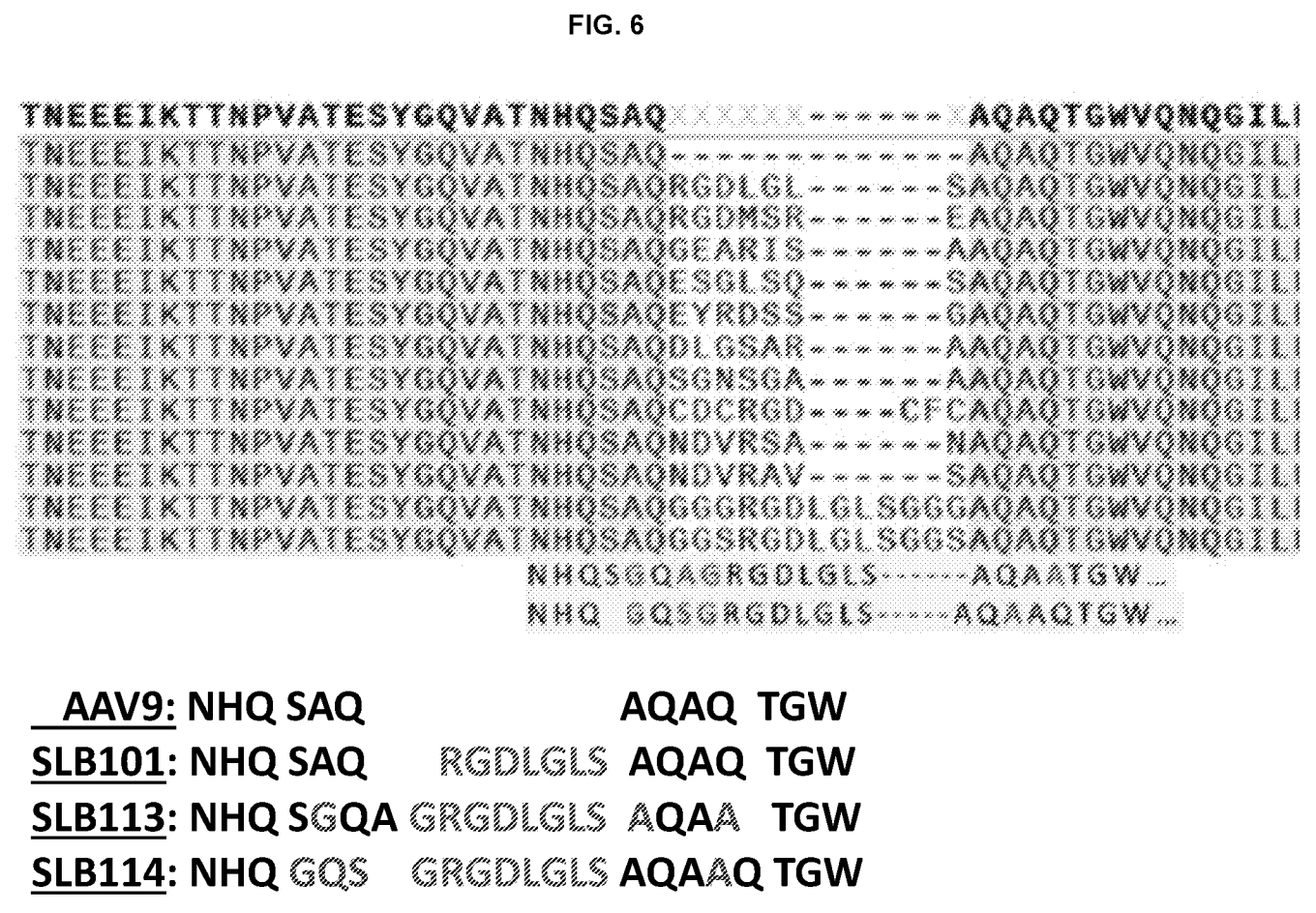

FIG. 6 shows sequence alignment of wild-type AAV9 and SLB101-SLB 114 (the 2nd to the 16th line, respectively) and the consensus sequence (top 1st line sequence). A smaller regional alignment among wild-type AAV9, SLB101, SLB-113, and SLB114 is also included.

Figure 7:
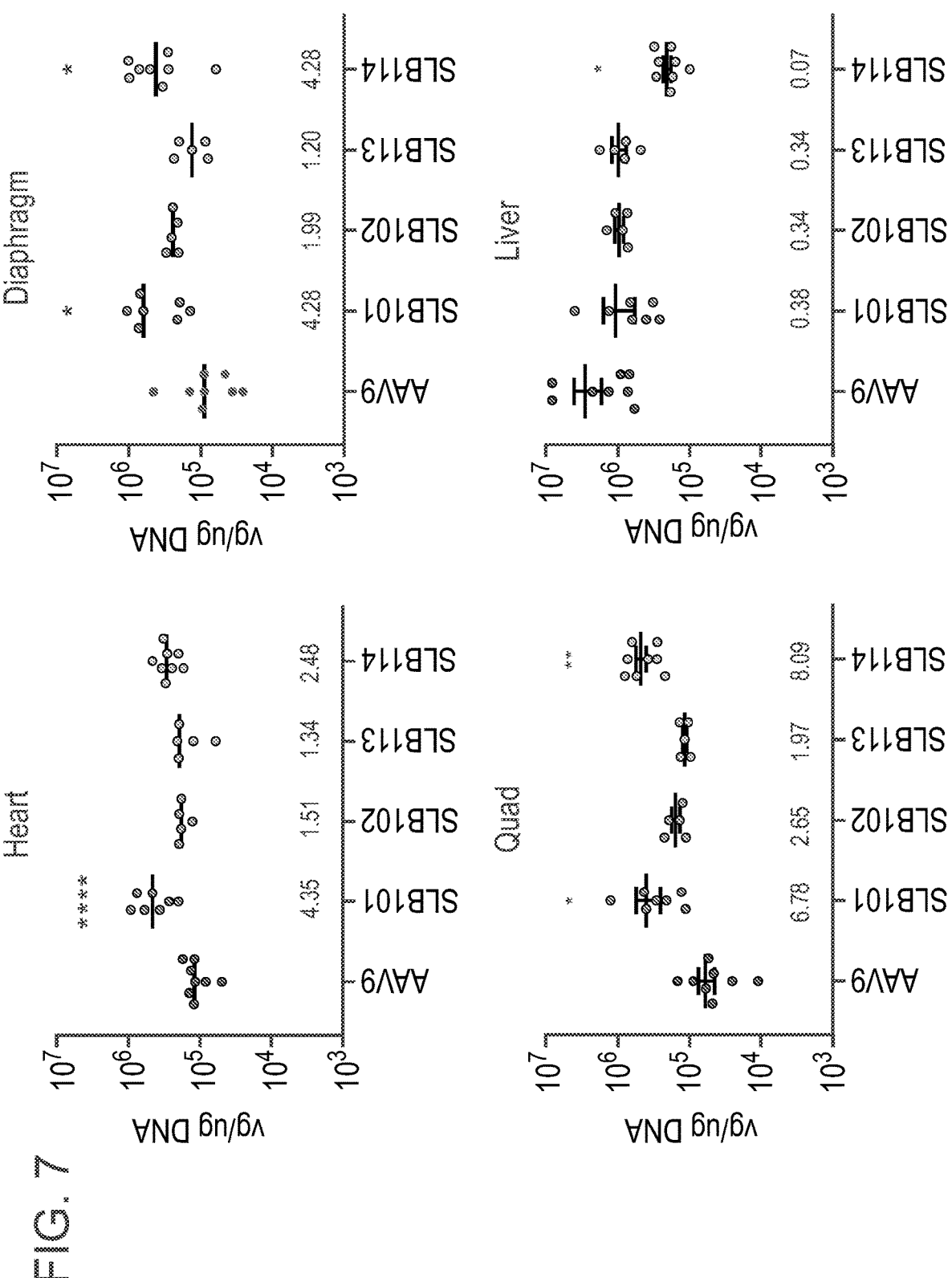

FIG. 7 shows biodistribution of AAV9 variant viruses with the variant capsids SLB-101, -102, -113, and -114 as compared to wild-type AAV9, in the heart, quad, and diaphragm muscles, as well as in the liver. Different levels of statistical significance are indicated with "*"

Figure 8:
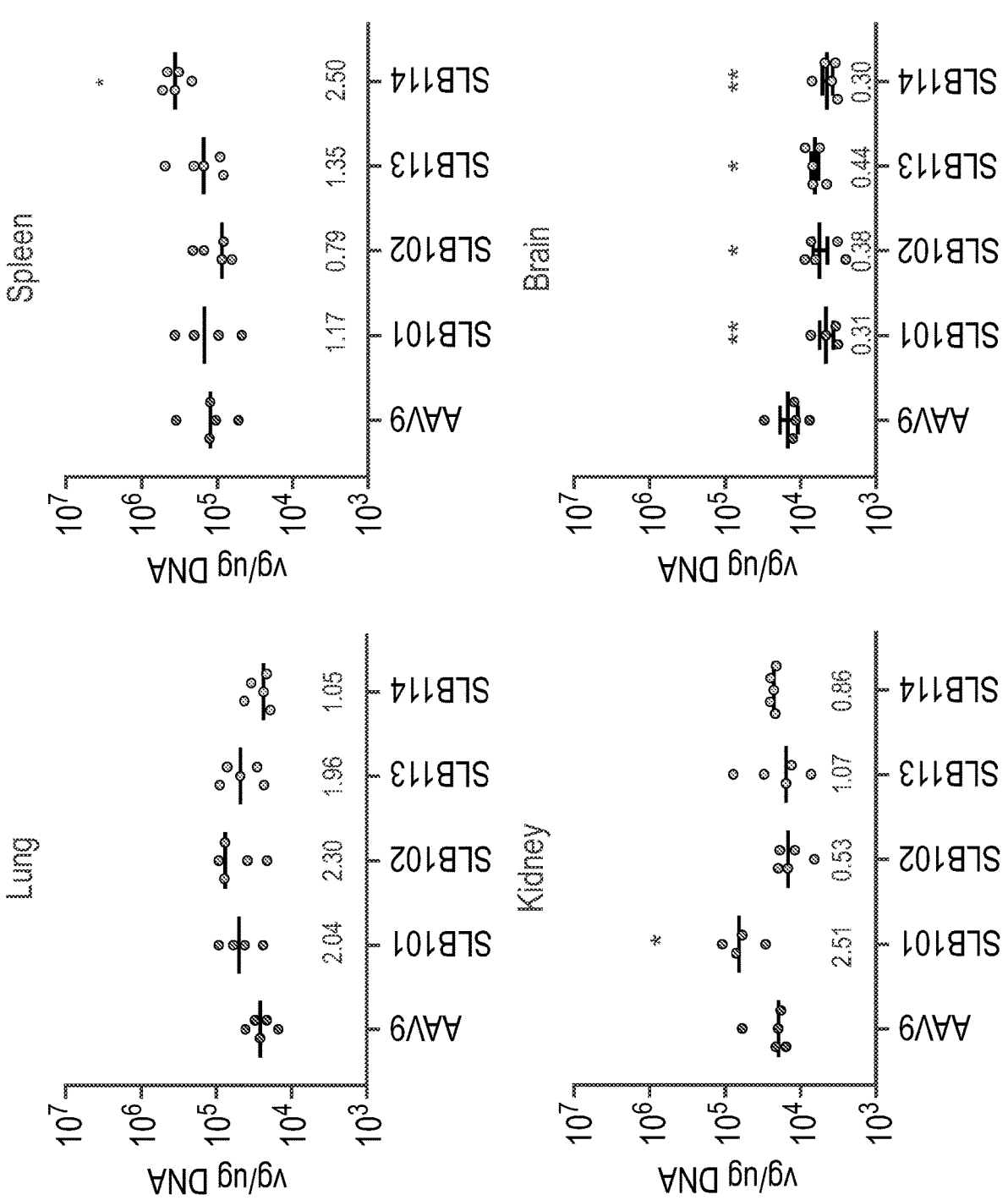

FIG. 8 shows extended biodistribution of AAV9 variant viruses with the variant capsids SLB-101, -102, -113, and -114 as compared to wild-type AAV9, in the lung, kidney, brain, and spleen. Different levels of statistical significance are indicated with "*"

Figure 9:
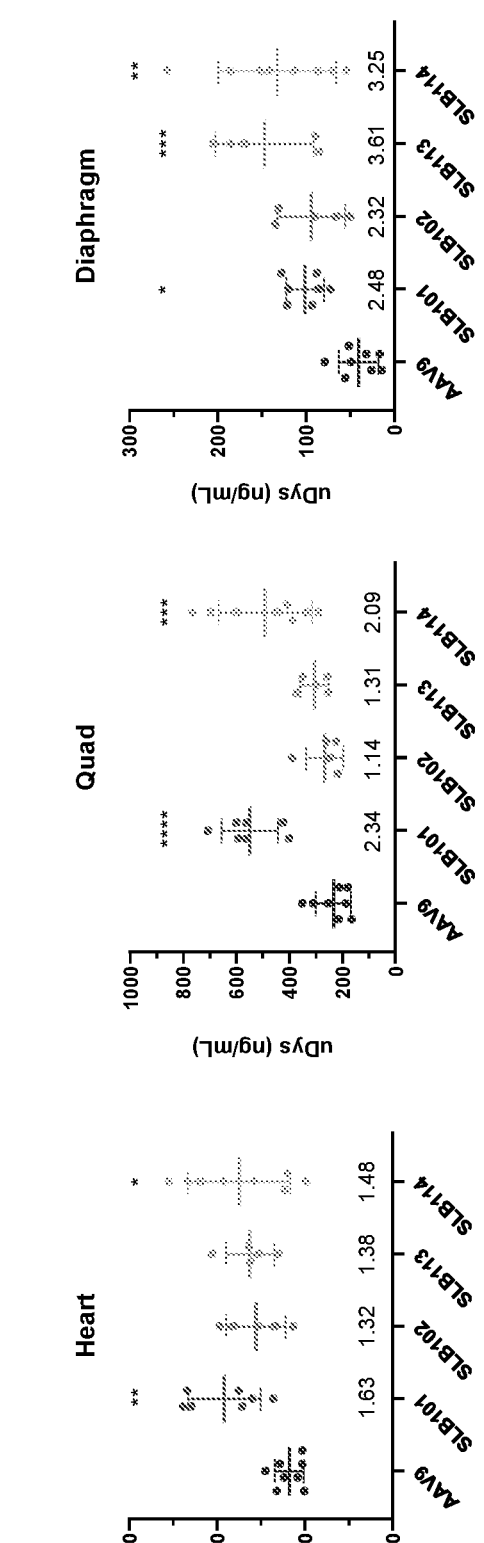

FIG. 9 shows expression of microdystrophin encoded by AAV9 vectors with the variant AAV9 capsids SLB-101, -102, -113, and -114, as compared to wild-type AAV9. Different levels of statistical significance are indicated with "*"

DETAILED DESCRIPTION OF THE INVENTION

1. Overview

The invention described herein provides an optimized delivery of gene of interest (GOI), partly based on an optimized rAAV capsid that exhibits superior biodistribution than wild-type capsids. Such rAAV having modified VPI capsids can be used to preferentially deliver GOI to muscle tissues at higher expression level and/or lower dose, thus facilitating more successful gene therapy targeting muscle tissues (e.g., skeletal, cardiac, and/or smooth muscle tissues).

In particular, according to one aspect of the invention, provided herein is modified AAV capsids and methods for AAV capsid selection that enable preferential targeted delivery of GOI to muscle tissues and muscle cell types.

According to another aspect of the invention, provided herein is a method for selecting a potent infectious AAV capsid for potential lowering of an effective AAV dose required for successful gene therapy.

As rAAV drug products advance clinically, analytical tools to characterize these complex products are needed. Examples include detection and quantification of mammalian cell host or viral helper DNA by PCR, qPCR, denaturing gel electrophoresis, and Southern blot. Development and validation of these and additional assays will enable full characterization of rAAV vectors. Thus yet another aspect of the invention provides an analytical tool for characterizing the subject rAAV capsids, vectors, and products, such as the ones described in the Examples.

A further aspect of the invention provides an in vitro potency assay as a critical tool for the development of the subject rAAV capsids and vectors. rAAV vectors with capsids of various natural serotypes and engineered capsids are compared to estimate their efficacy for systemic administration, and their potential for the development of treatment for disease indications treatable by gene therapy, such as Duchenne muscular dystrophy (DMD). In applications that require systemic administration of high doses of vectors, such as Duchenne muscular dystrophy, these analytical tools and assays have the potential to further characterize and improve rAAV products, and thereby improve safety and efficacy of gene transfer therapy.

The detailed aspects of the invention are described further below.

2. Modified VP1 Capsids

The modified AAV9 VP1 capsid protein of the invention has a short peptide of about 7-13 residues inserted between residues Q588 and A589 of the wild-type AAV9 VP1 capsid protein. In certain embodiments, the short peptide is any one of SEQ ID NOs: 1-12.

```
                                           (SEQ ID NO: 1)
       RGDLGLS
       (also known as SLB101)

(SEQ ID NO: 2)
       RGDMSRE
       (also known as SLB102)

(SEQ ID NO: 3)
       GEARISA
       (also known as SLB103)

(SEQ ID NO: 4)
       ESGLSQS
       (also known as SLB104)

(SEQ ID NO: 5)
       EYRDSSG
       (also known as SLB105)

(SEQ ID NO: 6)
       DLGSARA
       (also known as SLB106)

(SEQ ID NO: 7)
       SGNSGAA
       (also known as SLB107)

(SEQ ID NO: 8)
       CDCRGDCFC
       (also known as SLB108)

(SEQ ID NO: 9)
       NDVRSAN
       (also known as SLB109)

(SEQ ID NO: 10)
       NDVRAVS
       (also known as SLB110)

(SEQ ID NO: 11)
       GGGRGDLGLSGGG
       (also known as SLB111)

(SEQ ID NO: 12)
       GGSRGDLGLSGGS
       (also known as SLB112)
```

Two additional sequences with similar insertion modifications but different surrounding/flanking sequences are referred to as SLB113 and SLB114 (see FIG. 6).

Wiley-type AAV9 VP1 capsid protein sequence is known in the art, and is copied below. The residues Q588 and A589, between which one of SEQ ID NO: 1-12 is inserted, are double underlined.

(SEQ ID NO: 13)
MAADGYLPDWLEDNLSEGIREWWALKPGAPQPKANQQHQDNARGLVLPG

YKYLGPGNGLDKGEPVNAADAAALEHDKAYDQQLKAGDNPYLKYNHADA

EFQERLKEDTSFGGNLGRAVFQAKKRLLEPLGLVEEAAKTAPGKKRPVE

QSPQEPDSSAGIGKSGAQPAKKRLNFGQTGDTESVPDPQPIGEPPAAPS

GVGSLTMASGGGAPVADNNEGADGVGSSSGNWHCDSQWLGDRVITTSTR

TWALPTYNNHLYKQISNSTSGGSSNDNAYFGYSTPWGYFDFNRFHCHFS

PRDWQRLINNNWGFRPKRLNFKLFNIQVKEVTDNNGVKTIANNLTSTVQ

VFTDSDYQLPYVLGSAHEGCLPPFPADVEMIPQYGYLTLNDGSQAVGRS

SFYCLEYFPSQMLRTGNNFQFSYEFENVPFHSSYAHSQSLDRLMNPLID

-continued

QYLYYLSKTINGSGQNQQTLKFSVAGPSNMAVQGRNYIPGPSYRQQRVS

TTVTQNNNSEFAWPGASSWALNGRNSLMNPGPAMASHKEGEDRFFPLSG

SLIFGKQGTGRDNVDADKVMITNEEEIKTTNPVATESYGQVATNHQSA

QAQAQTGWVQNQGILPGMVWQDRDVYLQGPIWAKIPHTDGNFHPSPL

MGGFGMKHPPPQILIKNTPVPADPPTAFNKDKLNSFITQYSTGQVSVE

IEWELQKENSKRWNPEIQYTSNYYKSNNVEFAVNTEGVYSEPRPIGTRY

LTRNL

In certain embodiments, the modified AAV9 VP1 capsids of the invention has the polypeptide of SEQ ID NO: 1 (bold italic) inserted between residues Q588 and A589 (both double underlined) of SEQ ID NO: 13 as following:

(SEQ ID NO: 14)
MAADGYLPDWLEDNLSEGIREWWALKPGAPQPKANQQHQDNARGLVLPGYKYLGPGN

GLDKGEPVNAADAAALEHDKAYDQQLKAGDNPYLKYNHADAEFQERLKEDTSFGGNLGRAVE

QAKKRLLEPLGLVEEAAKTAPGKKRPVEQSPQEPDSSAGIGKSGAQPAKKRLNFGQTGDTES

VPDPQPIGEPPAAPSGVGSLTMASGGGAPVADNNEGADGVGSSSGNWHCDSQWLGDRVITTS

TRTWALPTYNNHLYKQISNSTSGGSSNDNAYFGYSTPWGYFDFNRFHCHESPRDWQRLINNN

WGFRPKRLNFKLFNIQVKEVTDNNGVKTIANNLTSTVQVFTDSDYQLPYVLGSAHEGCLPPF

PADVEMIPQYGYLTLNDGSQAVGRSSFYCLEYFPSQMLRTGNNFQFSYEFENVPFHSSYAHS

QSLDRLMNPLIDQYLYYLSKTINGSGQNQQTLKFSVAGPSNMAVQGRNYIPGPSYRQQRVST

TVTQNNNSEFAWPGASSWALNGRNSLMNPGPAMASHKEGEDRFFPLSGSLIFGKQGTGRDNV

DADKVMITNEEEIKTTNPVATESYGQVATNHQSAQ_RGDLGLS_AQAQTGW**VQNQGILPGMVWQ

DRDVYLQGPIWAKIPHTDGNFHPSPLMGGFGMKHPPPQILIKNTPVPADPPTAFNKDKLNSF

ITQYSTGQVSVEIEWELQKENSKRWNPEIQYTSNYYKSNNVEFAVNTEGVYSEPRPIGTRYL

TRNL

In certain embodiments, the modified AAV9 VP1 capsids of the invention has the polypeptide of SEQ ID NO: 11 (bold italic) inserted between residues Q588 and A589 (both double underlined) of SEQ ID NO: 13 as following:

(SEQ ID NO: 15)
MAADGYLPDWLEDNLSEGIREWWALKPGAPQPKANQQHQDNARGLVLPGYKYLGPGN

GLDKGEPVNAADAAALEHDKAYDQQLKAGDNPYLKYNHADAEFQERLKEDTSFGGNLGRAVE

QAKKRLLEPLGLVEEAAKTAPGKKRPVEQSPQEPDSSAGIGKSGAQPAKKRLNFGQTGDTES

VPDPQPIGEPPAAPSGVGSLTMASGGGAPVADNNEGADGVGSSSGNWHCDSQWLGDRVITTS

TRTWALPTYNNHLYKQISNSTSGGSSNDNAYFGYSTPWGYFDFNRFHCHFSPRDWQRLINNN

WGFRPKRLNFKLFNIQVKEVTDNNGVKTIANNLTSTVQVFTDSDYQLPYVLGSAHEGCLPPF

PADVFMIPQYGYLTLNDGSQAVGRSSFYCLEYFPSQMLRTGNNFQFSYEFENVPFHSSYAHS

QSLDRLMNPLIDQYLYYLSKTINGSGQNQQTLKFSVAGPSNMAVQGRNYIPGPSYRQQRVST

TVTQNNNSEFAWPGASSWALNGRNSLMNPGPAMASHKEGEDRFFPLSGSLIFGKQGTGRDNV

DADKVMITNEEEIKTTNPVATESYGQVATNHQSAQ_GGGRGDLGLSGGG_AQAQTGW**VQNQGIL

-continued

PGMVWQDRDVYLQGPIWAKIPHTDGNFHPSPLMGGFGMKHPPPQILIKNTPVPADPPTAENK

DKLNSFITQYSTGQVSVEIEWELQKENSKRWNPEIQYTSNYYKSNNVEFAVNTEGVYSEPRP

IGTRYLTRNL

In certain embodiments, the modified AAV9 VP1 capsids of the invention has the polypeptide of SEQ ID NO: 12 (bold italic) inserted between residues Q588 and A589 (both double underlined) of SEQ ID NO: 13 as following:

avoid redundancy). For example, in certain embodiments, the in vitro cell line is C2C12 or patient-derived Mouly cells. In certain embodiments, the in vivo assay is conducted in the mdx mouse model of DMD.

(SEQ ID NO: 16)
MAADGYLPDWLEDNLSEGIREWWALKPGAPQPKANQQHQDNARGLVLPGYKYLGPGN

GLDKGEPVNAADAAALEHDKAYDQQLKAGDNPYLKYNHADAEFQERLKEDTSFGGNLGRAVE

QAKKRLLEPLGLVEEAAKTAPGKKRPVEQSPQEPDSSAGIGKSGAQPAKKRLNFGQTGDTES

VPDPQPIGEPPAAPSGVGSLTMASGGGAPVADNNEGADGVGSSSGNWHCDSQWLGDRVITTS

TRTWALPTYNNHLYKQISNSTSGGSSNDNAYFGYSTPWGYFDENRFHCHESPRDWQRLINNN

WGFRPKRLNFKLFNIQVKEVTDNNGVKTIANNLTSTVQVFTDSDYQLPYVLGSAHEGCLPPF

PADVFMIPQYGYLTLNDGSQAVGRSSFYCLEYFPSQMLRTGNNFQFSYEFENVPFHSSYAHS

QSLDRLMNPLIDQYLYYLSKTINGSGQNQQTLKFSVAGPSNMAVQGRNYIPGPSYRQQRVST

TVTQNNNSEFAWPGASSWALNGRNSLMNPGPAMASHKEGEDRFFPLSGSLIFGKQGTGRDNV

DADKVMITNEEEIKTTNPVATESYGQVATNHQSAQ*GGSRGDLGLSGGS*AQAQTGW*VQNQGIL

PGMVWQDRDVYLQGPIWAKIPHTDGNFHPSPLMGGFGMKHPPPQILIKNTPVPADPPTAFNK

DKLNSFITQYSTGQVSVEIEWELQKENSKRWNPEIQYTSNYYKSNNVEFAVNTEGVYSEPRP

IGTRYLTRNL

The modified AAV9 VP1 capsids of the invention enable preferential targeted expression of GOI from rAAV packaged in such modified AAV9 VP1 capsids, especially in muscle tissues, including cardiac muscles (i.e., muscles in the heart), skeletal muscles (e.g., the quadriceps), and/or smooth muscles (e.g., the diaphragm muscles).

While not wishing to be bound by any particular theory, changing the wild-type amino acid sequences in the AAV9 VP1 capsid sequence around the insertion point (i.e., 1, 2, 3, 4, 5, 6, 7, or 8 residues N-terminal to Q588 and/or Q588 itself, and/or 1, 2, 3, 4, 5, 6, 7, or 8 residues C-terminal to A589 and/or A589 itself) may affect (e.g., adversely affect) tissue targeting and/or expression level of the GOI in the target tissue. One embodiment of this affect or change may be the tissue infection rate or expression level in a desirable and particular tissue(s), e.g., any of the muscle tissues such as cardiac, skeletal, and/or smooth muscle tissue(s), when compared with the AAV packaged with the subject modified AAV9 VP1 capsids that have completely preserved the wild-type AAV9 VPI capsid sequences around and including residues Q588 and A589.

In certain embodiments, the preferential expression of the GOI, compared to an otherwise identical rAAV construct except for using wild-type AAV9 capsids, is at least 50% higher, 100% higher (i.e., 2-fold), 3-fold, 5-fold, 10-fold, 12-fold, 15-fold, 20-fold, 22-fold, 25-fold, 30-fold, 50-fold, 75-fold, or 100-fold or more. In certain embodiments, the fold increase is measured based on an in vitro assay and/or an in vivo assay substantially as those described in the Examples (incorporated here by reference for clarity and to In certain embodiments, the modified adeno-associate virus (mAAV) capsid polypeptide is based not on AAV9, but on wild-type sequence of a non-AAV9 wild-type Clad F (e.g., AAVhu.32), a wild-type Clad A (e.g., AAV6), or a wild-type Clad E (e.g., AAV8, AAVrh.10, or AAVrh.74) VP1 capsid. That is, the polypeptide selected from the group consisting of SEQ ID NOs: 1-12 is inserted between the two corresponding residues of a non-AAV9 wild-type Clad F (e.g., AAVhu.32), a wild-type Clad A (e.g., AAV6), or a wild-type Clad E (e.g., AAV8, AAVrh.10, or AAVrh.74) VP1 capsid.

As used herein, "corresponding residues" refers to the residues in a non-AAV9 wild-type Clad F AAV (e.g., AAVhu.32), a wild-type Clad A AAV (e.g., AAV6), or a wild-type Clad E AAV (e.g., AAV8, AAVrh.10, AAVrh.37, or AAVrh.74) VP1 capsid that aligns with wild-type AAV9 VPI capsid residues 588 and 589, respectively.

As used herein, a non-AAV9 wild-type Clad F AAV includes AAVhu.32. A wild-type Clad A AAV includes AAV1/6, AAVhu.48R2, AAVhu.48R3, and AA Vhu.44R3. A wild-type Clad E AAV includes AAV8, AAVhu.37, AAVrh. 10, AAVpi.2, AAVrh.64R1, AAVrh.64R2, AAVrh.2R, AAVrh.74, and AAVrh.43.

For example, the insertion points in the representative Clad A AAV6, Clad E AAV8 and AAVrh.74, and Clad F AAV9 and AAVhu.32 are shown below. Note that due to the sequence difference, AAV8 residues N590 and T591 "corresponds to the AAV9 residues Q588 and A589, respectively.

| AAV9 (Clad F) | NHQSAQ$^{588}$_$^{589}$AQAQTGW |
|---|---|
| AAV8 (Clad E) | NLQQQN$^{590}$_$^{591}$TAPQIGT |
| AAVrh.10 (Clad E) | NLQQQN$^{590}$_$^{591}$AAPIVGA |
| AAVrh.74 (Clad E) | NLQQQN$^{590}$_$^{591}$AAPIVGA |
| AAVrh.37 (Clad E) | NLQQQN$^{590}$_$^{591}$TGPIVGN |
| AAV6 (Clad A) | NLQSSS$^{588}$_$^{589}$TDPATGD |

3. Gene of Interest (GOI) in rAAV and Treatable Diseases

The recombinant AAV vectors of the invention having the modified VPI capsids may carry any gene of interest (GOI) for treating a disease or condition through gene therapy. The GOI can be any gene or coding sequence within the packaging capacity of the rAAV, e.g., about 4-5 kb, or about 4.7 kb including the ITR sequences, or about 4.4 kb without accounting for the ITR sequences.

In certain embodiments, the rAAV carrying the GOI can be used in gene therapy to treat a disease or condition caused by lacking of function of an endogenous gene in the host, such as a defective version of the GOI.

As used herein, "gene of interest" or GOI generally refers to a nucleic acid or polynucleotide sequence, such as a gene, an open reading frame (ORF), or a coding sequence for protein or RNA such as siRNA, miRNA, shRNA, etc. However, in certain circumstances or context, the term GOI also loosely refers to a protein (encoded by the GOI), or a disease or indication that can be remedied by the GOI, or a disease or indication can be (but is not necessarily) caused by loss of function of the GOI.

For example, the gene GALGT2 encodes the protein GalNAc transferase ($\beta$-1,4-N-acetylgalactosamine galacto-syltransferase), which is an enzyme that transfers a complex sugar molecule onto a few specific proteins, including dystroglycan. Under normal circumstances, GalNAc transferase is found only at the neuromuscular junction (NMJ), where some components of the dystroglycan-associated protein complex are different than elsewhere in muscle. Importantly, at the NMJ, utrophin is present instead of dystrophin. In the mdx mouse model of muscular dystrophy, viral gene transfer of GALGT2 results in expression of GalNAc transferase across the entire muscle membrane, instead of just at the normal expression domain of the NMJ, as well as upregulation of utrophin across the entire muscle fiber. In the mdx mouse, this expression can correct muscle functional deficits to the same degree as does microdystrophin gene expression. Furthermore, overexpression of GALGT2 corrects muscle pathology in mouse models of other muscular dystrophies, including LGMD2A and congenital muscular dystrophy (MDCIA). Thus GALGT2 is a GOI for treating muscular dystrophy such as DMD, BMD, LGMD2A and MDCIA, even though GALGT2 is not necessarily defective per se in the patient in need of treatment.

In another example, Sarcolipin (SLN) inhibits the sarco/ endoplasmic reticulum (SR) Ca$^{2+}$ ATPase (SERCA), and is abnormally elevated in the muscle of DMD patients and animal models such as the mdx mouse model of DMD. Reducing SLN levels by AAV9-mediated RNA interference ameliorates dystrophic pathology in the severe dystrophin/ utrophin double mutant (mdx:utr) mouse model of DMD, including attenuation of muscle pathology and improvement of diaphragm, skeletal muscle and cardiac function. Thus the coding sequence for SLN RNAi is a GOI that remedies DMD.

Thus the GOI can be a gene (or protein) that, when expressed, replaces a mutated, damaged, or inactive gene or protein. The GOI can be a gene (or protein) that, when expressed, assists an already functioning process that requires modification for therapy in a disease, disorder, or dysfunction. The GOI can be a gene (or protein) that, when expressed, assists a dysfunctional process that requires modification for therapy in a disease, disorder, or dysfunction. A GOI nucleic acid sequence can be DNA, RNA, or synthetic nucleic acid molecule. The GOI can be a protein, an enzyme, a structural protein, a functional protein, or an adaptable protein based on cell function(s). The GOI can provide therapeutic benefit or a treatment modality for a disease, disorder, or dysfunction.

In certain embodiments, the GOI may be CRISPR-Cas9, Cas 13, TALEN, or other genetic based gene editing protein that are required for intracellular delivery for their intended activity.

Any and all GOIs as used herein may require codon optimization for enhanced expression and activity via known computer based algorithms.

Thus the rAAV that may be produced by using the subject viral capsids (e.g., modified VPI capsids) and may encode a gene of interest (GOI) useful for, e.g., gene therapy to treat a disease or condition. Representative (non-limiting) gene of interest (GOI) may include: a gene responsible for/defective in LGMD2E (limb-girdle muscular dystrophy type 2E), LGMD2D (limb-girdle muscular dystrophy type 2D), LGMD2C (limb-girdle muscular dystrophy type 2C), LGMD2B (limb-girdle muscular dystrophy type 2B), LGMD2L (limb-girdle muscular dystrophy type 2L), LGMD2I (limb-girdle muscular dystrophy type 21), or a gene or coding sequence for NAGLU ($\alpha$-N-acetylglu-cosaminidase, for Sanfilippo syndrome or mucopolysaccharidosis type IIIB (MPS IIIB)), sulfamidase or SGSH (for mucopolysaccharidosis type IIIA or MPS IIIA), Factor IX, Factor VIII, Myotubularin 1 (MTM1), Survival of Motor Neuron (SMN, for spinal muscular atrophy or SMA), Gal-NAc transferase GALGT2, calpain-3 (CAPN-3), acid alpha-glucosidase (GAA, for Pompe disease), alpha-galactosidase A or GLA (for Fabry disease), glucocerebrosidase, dystrophin or microdystrophin.

In certain embodiments, the GOI is a microdystrophin gene.

In certain embodiments, the microdystrophin gene is any one described in the following patents: U.S. Pat. Nos. 7,906,111; 7,001,761; 7,510,867; 6,869,777; 8,501,920; 7,892,824; PCT/US2016/013733; U.S. Pat. No. 10,166,272 (all incorporated herein by reference). In certain embodiments, the microdystrophin gene is capable of being packaged into a rAAV virion, e.g., no more than about 4.7 kb in size.

In certain embodiments, the microdystrophin gene contains within its coding sequence spectrin-like repeats R16 and R17 that are capable of restoring nitric oxide synthase (nNOS) activity to the sarcolemma (such as those described in U.S. Pat. No. 7,892,824).

In certain embodiments, the microdystrophin gene comprises a coding sequence for the R1, R16, R17, R23, and R24 spectrin-like repeats (i.e., SR1, SR16, SR17, SR23, and SR24, respectively) of the full-length dystrophin protein, such as one described in PCT/US2016/013733 (incorporated herein by reference). In certain embodiments, the microdystrophin gene does not encode any other spectrin repeats of
the full-length dystrophin protein, other than SR1, SR16,
SR17, SR23, and SR24.

In certain embodiments, the microdystrophin gene is
described in U.S. Pat. Nos. 7,906,111; 7,001,761; 7,510,867;
6,869,777; 8,501,920; 7,892,824; or U.S. Pat. No. 10,166,
272, or in PCT/US2016/013733 (all incorporated herein by
reference). For example, PCT/US2016/013733 (WO2016/
115543A2) provides a micro-dystrophin gene operatively
connected to a regulatory cassette, wherein the micro-
dystrophin gene encodes a protein comprising: an amino-
terminal actin-binding domain; a β-dystroglycan binding
domain; and a spectrin-like repeat domain, comprising at
least four spectrin-like repeats, wherein two of the at least
four spectrin-like repeats comprise a neuronal nitric oxide
synthase binding domain. In certain embodiments, the at
least four spectrin-like repeats include spectrin-like repeat 1
(SR1), spectrin-like repeat 16 (SR16), spectrin-like repeat
17 (SR17), and spectrin-like repeat 24 (SR24). In certain
embodiments, the protein encoded by the micro-dystrophin
gene further comprises at least a portion of a hinge domain,
such as at least one of a Hinge 1 domain, a Hinge 2 domain,
a Hinge 3 domain, a Hinge 4 domain, and a hinge-like
domain. In certain embodiments, the micro-dystrophin gene
comprises, in N- to C-terminal order: a Hinge 1 domain
(H1); a spectrin-like repeat 1 (SR1); a spectrin-like repeat 16
(SR16); a spectrin-like repeat 17 (SR17); a spectrin-like
repeat 24 (SR24); and a Hinge 4 domain (H4). In certain
embodiments, H1 is directly coupled to the SR1. In certain
embodiments, SR 1 is directly coupled to SR16. In certain
embodiments, SR16 is directly coupled to SR17. In certain
embodiments, SR 17 is directly coupled to SR24. In certain
embodiments, SR24 is directly coupled to the H4. In certain
embodiments, the protein encoded by the micro-dystrophin
gene further comprises between SR1 and SR16, in N- to
C-terminal order, a spectrin-like repeat 2 (SR2) and a
spectrin-like repeat 3 (SR3). In certain embodiments, SR1 is
directly coupled to SR2 and SR2 is further coupled to SR3.
In certain embodiments, H1 is directly coupled to SR1, SR1
is directly coupled to SR16, SR16 is directly coupled to
SR17, SR17 is directly coupled to SR23, SR23 is directly
coupled to SR24, and SR24 is directly coupled to H4.

In certain embodiments, the regulatory cassette is selected
from the group consisting of a CK8 promoter and a cardiac
troponin T (cTnT) promoter. In certain embodiments, the
protein encoded by the micro-dystrophin gene has between
five spectrin-like repeats and eight spectrin-like repeats. In
certain embodiments, the protein encoded by the micro-
dystrophin gene has at least 80% or 90% sequence identity
to the amino acid sequence of SEQ ID NO: 4 or 5 in
WO2016/115543A2 (incorporated herein by reference).

Diseases or conditions having a potential to benefit from
the rAAV comprising the subject modified VPI capsids
include: Huntington's disease, X-linked myotubular myopa-
thy (XLMTM), Acid maltase deficiency (e.g., Pompe dis-
ease), Spinal Muscular Atrophy (SMA), Myasthenia Gravis
(MG), Amyotrophic lateral sclerosis (ALS), Friedreich's
ataxia, Mitochondrial myopathy, Muscular dystrophies
(Duchenne's muscular dystrophy, Myotonic dystrophy,
Becker muscular dystrophy (BMD), Limb-girdle muscular
dystrophy (LGMD), Facioscapulohumeral muscular dystro-
phy (FSH), Congenital muscular dystrophy (CDM), Oculo-
pharyngeal muscular dystrophy (OPMD), Distal muscular
dystrophy, Emery-Dreifuss muscular dystrophy (EDMD),
Mucopolysaccharidoses (MPS), Metachromatic leukodys-
trophy (MLD), Batten Disease, Rett Syndrome, Krabbe
Disease, Canavan disease, X-Linked Retinoschisis, Achro-

14 matopsia (CNGB3 and CNGA3), X-Linked Retinitis Pig-
mentosa, Age-Related Macular Degeneration, neovascular-
ized macular degeneration, Pompe, Fabry's disease, MPS I,
II, IIIA, IIIB, Gaucher's disease, Dannon Disease, AlAt
Deficiency, Friedreich ataxia, Wilson's Disease, Batten Dis-
ease (CLN1, CLN3, CLN6, CLN8), Wolman Disease, Tay-
Sachs, Niemann-Lick Type C, CDKL5 deficiency Disorder,
B-thalassemia, Sickle cell disease.

In certain embodiments, diseases or conditions having a
potential to benefit from the rAAV of the invention may
include: Becker muscular dystrophy (BMD), Congenital
muscular dystrophies (CMD), Bethlem CMD, Fukuyama
CMD, Muscle-eye-brain diseases (MEBs), Rigid spine syn-
dromes, Ullrich CMD, Walker-Warburg syndromes (WWS),
Duchenne muscular dystrophy (DMD), Emery-Dreifuss
muscular dystrophy (EDMD), Facioscapulohumeral muscu-
lar dystrophy (FSHD), Limb-girdle muscular dystrophies
(LGMD), Myotonic dystrophy (DM), Oculopharyngeal
muscular dystrophy (OPMD), Motor neuron diseases
including ALS (amyotrophic lateral sclerosis), Spinal-bulbar
muscular atrophy (SBMA), Spinal muscular atrophy
(SMA).

In certain embodiments, diseases or conditions having a
potential to benefit from the rAAV of the invention may
include ion channel diseases, which are typically marked by
muscular weakness, absent muscle tone, or episodic muscle
paralysis. They include Andersen-Tawil syndrome, Hyper-
kalemic periodic paralysis, Hypokalemic periodic paralysis,
Myotonia congenita, Becker myotonia, Thomsen myotonia,
Paramyotonia congenita, Potassium-aggravated myotonia.

In certain embodiments, diseases or conditions having a
potential to benefit from the rAAV of the invention may
include mitochondrial diseases, which occur when structures
that produce energy for a cell malfunction. Such diseases
include: Friedreich's ataxia (FA), Mitochondrial myopa-
thies, Kearns-Sayre syndrome (KSS), Leigh syndrome (sub-
acute necrotizing encephalomyopathy), Mitochondrial DNA
depletion syndromes, Mitochondrial encephalomyopathy,
lactic acidosis and stroke-like episodes (MELAS), Mito-
chondrial neurogastrointestinal encephalomyopathy (MN-
GIE), Myoclonus epilepsy with ragged red fibers (MERRF),
Neuropathy, ataxia and retinitis pigmentosa (NARP), Pear-
son syndrome, Progressive external opthalmoplegia (PEO).

In certain embodiments, diseases or conditions having a
potential to benefit from the rAAV of the invention may
include myopathies, which is a disease of muscle in which
the muscle fibers do not function properly, resulting in
muscular weakness. Myopathies include: Cap myopathies,
Centronuclear myopathies, Congenital myopathies with
fiber type disproportion, Core myopathies, Central core
disease, Multiminicore myopathies, Myosin storage myopa-
thies, Myotubular myopathy, Nemaline myopathies, Distal
myopathies, GNE myopathy/Nonaka myopathy/hereditary
inclusion-body myopathy (HIBM), Laing distal myopathy,
Markesberg-Griggs late-onset distal myopathy, Miyoshi
myopathy, Udd myopathy/tibial muscular dystrophy, Vocal
cord and pharyngeal distal myopathy, Welander distal
myopathy, Endocrine myopathies, Hyperthyroid myopathy,
Hypothyroid myopathy, Inflammatory myopathies, Derma-
tomyositis, Inclusion-body myositis, Polymyositis, Meta-
bolic myopathies, Acid maltase deficiency (AMD, Pompe
disease), Carnitine deficiency, Carnitine palmityl transferase
deficiency, Debrancher enzyme deficiency (Cori disease,
Forbes disease), Lactate dehydrogenase deficiency, Myoad-
enylate deaminase deficiency, Phosphofructokinase defi-
ciency (Tarui disease), Phosphoglycerate kinase deficiency,

US 12,653,909 B2

15

Phosphoglycerate mutase deficiency, Phosphorylase deficiency (McArdle disease), Myofibrillar myopathies (MFM), Scapuloperoncal myopathy.

In certain embodiments, diseases or conditions having a potential to benefit from the rAAV of the invention may include neuromuscular junction diseases, which result from the destruction, malfunction or absence of one or more key proteins involved in the transmission of signals between muscles and nerves. Such diseases include: Congenital myasthenic syndromes (CMS), Lambert-Eaton myasthenic syndrome (LEMS), Myasthenia gravis (MG).

In certain embodiments, diseases or conditions having a potential to benefit from the rAAV of the invention may include peripheral nerve diseases, in which the motor and sensory nerves that connect the brain and spinal cord to the rest of the body are affected, causing impaired sensations, movement or other functions. Such diseases include: Charcot-Marie-Tooth disease (CMT), Giant axonal neuropathy (GAN), muscle wasting in cachexia and aging.

4. Production of rAAV

The rAAV having the modified VPI capsids of the invention can be produced by using any standard rAAV production methods, typically using a producer cell line, so long as the method/producer cell line is modified to provide the modified VPI capsid proteins in place of (or at least in addition to) the wild-type VPI capsids.

A number of strategies differing in principles have been used for rAAV production, all of which can be used to produce the subject rAAV.

In certain embodiments, the subject rAAV is produced based on the helper-virus-free transient transfection method, with all cis and trans components (vector plasmid and packaging plasmids, along with helper genes isolated from adenovirus) in suitable host cells such as 293 cells. The transient-transfection method is simple in vector plasmid construction and generates high-titer AAV vectors that are free of adenovirus. The modified VP1 capsid proteins can be encoded by one of the plasmids used in transient transfection of the producer cell line.

In certain embodiments, the subject rAAV is produced using a recombinant herpes simplex virus (rHSV)-based AAV production system, which utilizes rHSV vectors to bring the AAV vector and the Rep and Cap genes (i.e., the modified VPI capsid gene of the invention) into the producer cells. The modified cap gene can be present in the rHSV vector that may also hosts the rAAV genome.

In certain embodiments, the subject rAAV is produced using a baculovirus system that requires simultaneous infection of insect cells with several baculovirus vectors to deliver the AAV vector cassette and the Rep and Cap genes (i.e., the modified VPI capsid gene of the invention).

In certain embodiments, the subject rAAV is produced based on certain AAV producer cell lines derived from, e.g., HeLa or A549 or HEK293 cells, which stably harbored AAV Rep/cap genes (i.e., the modified VPI capsid gene of the invention). The AAV vector cassette can either be stably integrated in the host genome or be introduced by an adenovirus that contained the cassette.

In certain embodiments, such producer cell line for rAAV production comprises an rAAV provirus that encodes the GOI flanked by the AAV ITR sequences, wherein the rAAV provirus is integrated into the genome of the producer cell line for rAAV production.

5. Treatment of Muscular Dystrophy Using rAAV

The subject rAAV comprising the modified VPI capsids of the invention can be used in gene therapy for treating various forms of muscular dystrophy, such as Duchenne's muscular dystrophy (DMD), Myotonic dystrophy, Becker muscular dystrophy (BMD), Limb-girdle muscular dystrophy (LGMD), Facioscapulohumeral muscular dystrophy (FSH), Congenital muscular dystrophy (CDM), Oculopharyngeal muscular dystrophy (OPMD), Distal muscular dystrophy, Emery-Dreifuss muscular dystrophy (EDMD), etc. In certain embodiments, the muscular dystrophy is DMD or BMD.

Thus one aspect of the invention provides a method of treating muscular dystrophy (such as DMD and BMD) in a subject in need thereof, the method comprising administering to the subject a therapeutically effective amount of a recombinant AAV (rAAV) vector encoding a functional version of the gene defective in the muscular dystrophy, such as a microdystrophin gene, wherein the rAAV comprises any of the modified VPI capsid proteins of the invention.

In certain embodiments, the microdystrophin gene is one described in U.S. Pat. Nos. 7,906,111; 7,001,761; 7,510,867; 6,869,777; 8,501,920; 7,892,824; PCT/US2016/013733; or U.S. Pat. No. 10,166,272 (all incorporated herein by reference).

In certain embodiments, the microdystrophin gene comprises a coding sequence for the R1, R16, R17, R23, and R24 spectrin-like repeats of the full-length dystrophin protein (such as one described in PCT/US2016/013733).

In certain embodiments, the method further comprises producing the subject rAAV prior to administering to the subject the rAAV so produced.

EXAMPLES

Example 1 In Vitro Assays Comparing the Subject AAV-SLB101 to AAV9 and AAV8

This experiment compares the effect of the subject rAAV capsid on expression of a GOI from a recombinant AAV vector in a muscle cell, in comparison to that of AAV8 and AAV9.

In particular, C2C12 cells—immortalized mouse myoblast cell line cells—were transduced at three multiplicities of infection (MOIs) with microdystrophin-expressing rAAV vectors packaged in AAV9, AAV8, and the subject capsid AAV-SLB101 (SEQ ID NO: 14), respectively. Cells were harvested 72 hours after transduction, and microdystrophin expression was measured by ELISA. The data were shown in FIGS. 1A-1C, with mean±SD for each data point in FIGS. 1A and 1B. Statistical significance was determined by one-way ANOVA test in comparison to AAV9 data at each MOI.

Figure 1A:
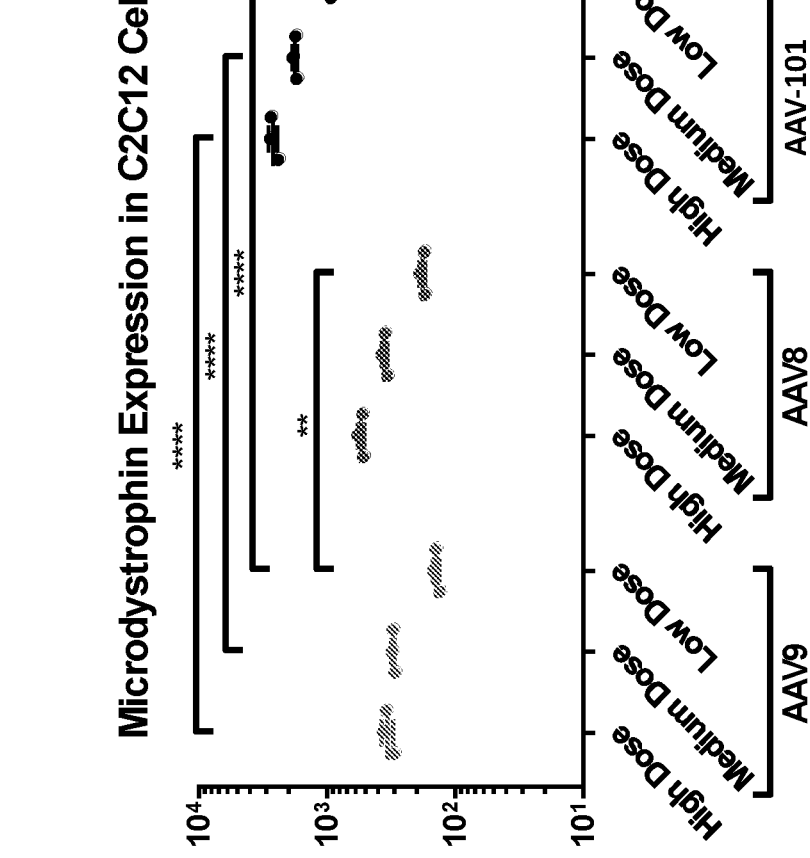
FIGS. 1A-1E show in vitro potency assay comparing AAV9 and AAV8 with the subject AAV-SLB101 capsid (abbreviated in the figures as "AAV-101" or referred to as "SLB101," "SLB-101" or variations thereof elsewhere).

In FIG. 1A, microdystrophin expression was determined based on micrograms (μg) of expressed microdystrophin per mL. The data shows that the subject rAAV capsid was associated with much higher expression of the GOI (e.g., microdystrophin) in C2C12 muscle cells compared to AAV9 capsid. Although no direct statistical comparison has been made, the data also suggests that the subject rAAV capsid was also associated with much higher expression of the GOI (e.g., microdystrophin) in C2C12 muscle cells compared to AAV8 capsid.

Figure 1B:
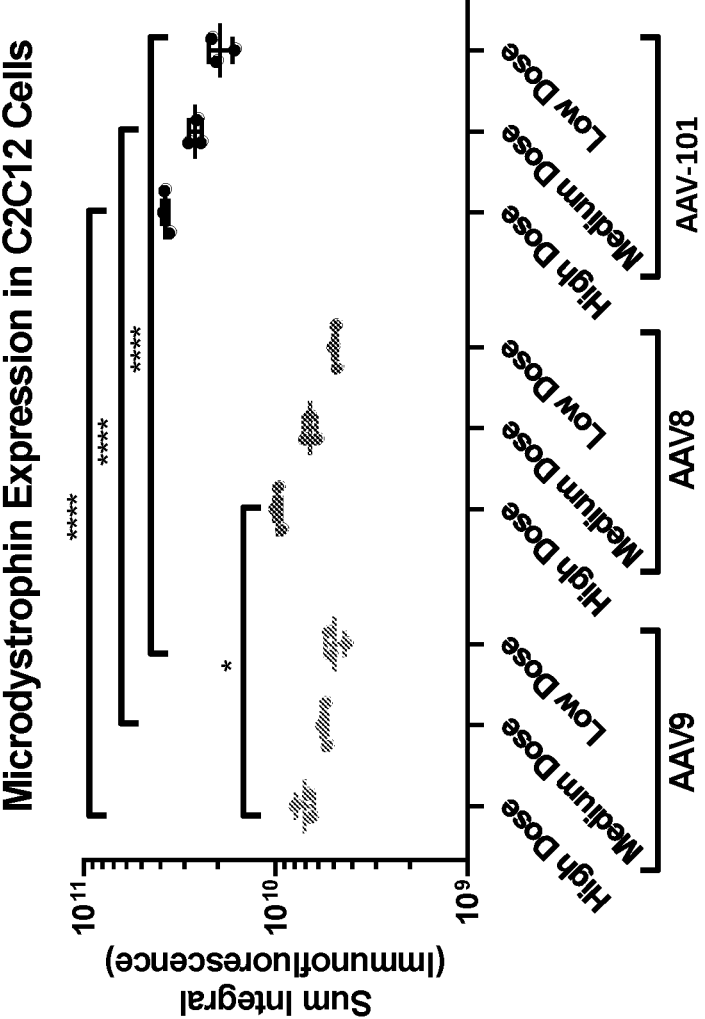

In FIG. 1B, microdystrophin expression was determined based on sum integral of immunofluorescence intensity. The data again shows that the subject rAAV capsid was associated with much higher expression of the GOI (e.g., microdystrophin) in C2C12 muscle cells compared to AAV9 capsid. Although no direct statistical comparison has been made, the data also suggests that the subject rAAV capsid was also associated with much higher expression of the GOI (e.g., microdystrophin) in C2C12 muscle cells compared to AAV8 capsid.

Figure 1C:
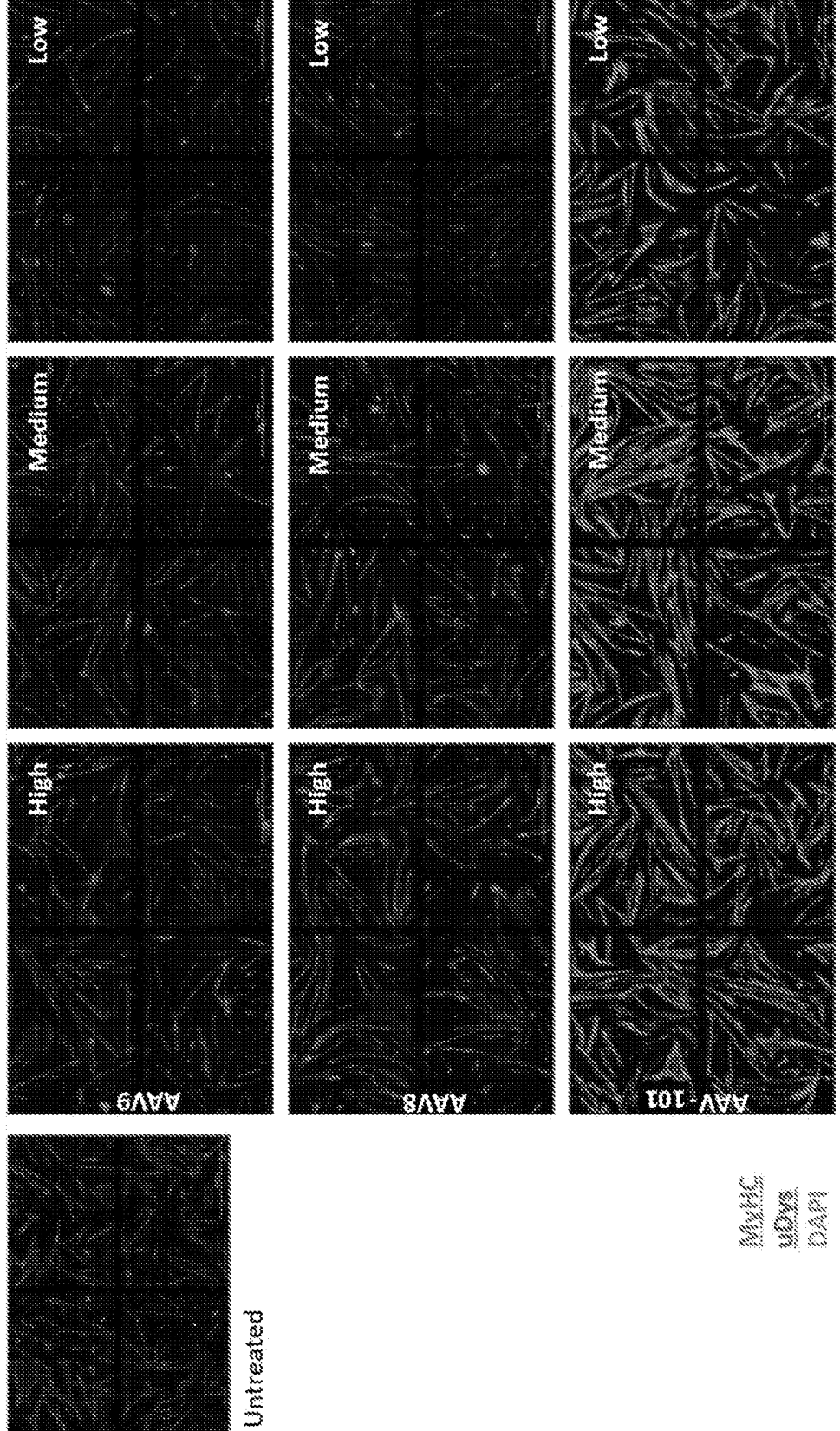

In FIG. 1C, C2C12 cells were similarly transduced at three multiplicities of infection (MOIs) with microdystrophin-expressing rAAV vectors packaged in AAV9, AAV8, and the subject capsid AAV-SLB101, respectively. Cells were fixed and immunostained 72 hours after transduction, and microdystrophin expression was visualized by immunofluorescence (IF). Uninfected/untreated cells were stained with green fluorescence against Myosin heavy chain (MyHC). Cell nuclei were stained with DAPI. The data visually confirms the superior ability of the subject rAAV capsid to direct expression of the GOI (e.g., microdystrophin) in C2C12 muscle cells compared to both the AAV9 and AAV8 capsids, at all dose levels tested.

Figure 1D:
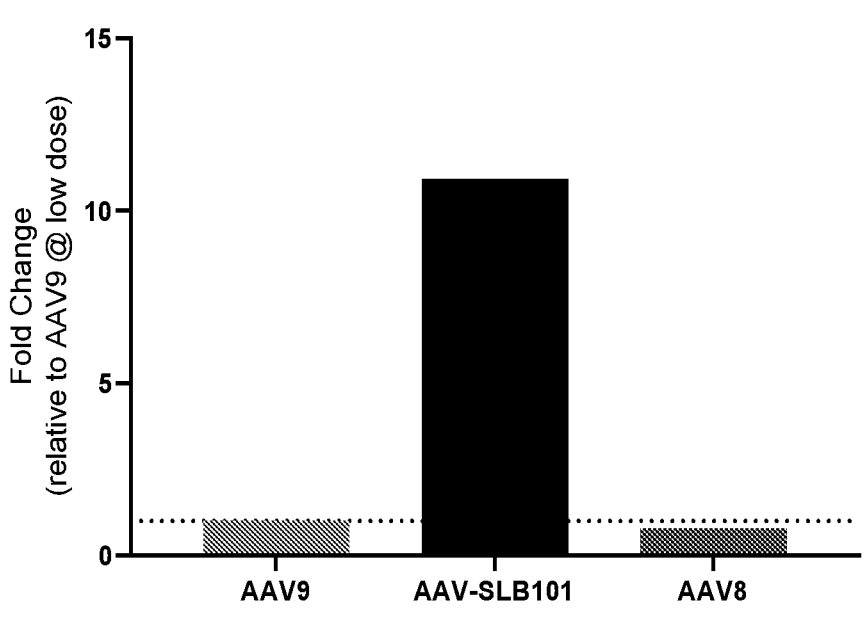

In another experiment, C2C12 cells were transduced with the same three AAVs above, but at the lowest MOI only. Cells were harvested 96 hours after transduction, and microdystrophin expression was measured. The data were then normalized to that of AAV9 and plotted in FIG. 1D, and fold change was indicated in the table insert in FIG. 1D. It is apparent that AAV-SLB101 has significantly higher microdystrophin protein expression than AAV9 ($p<0.0001$). Statistics were determined by ordinary one-way ANOVA.

Figure 1E:
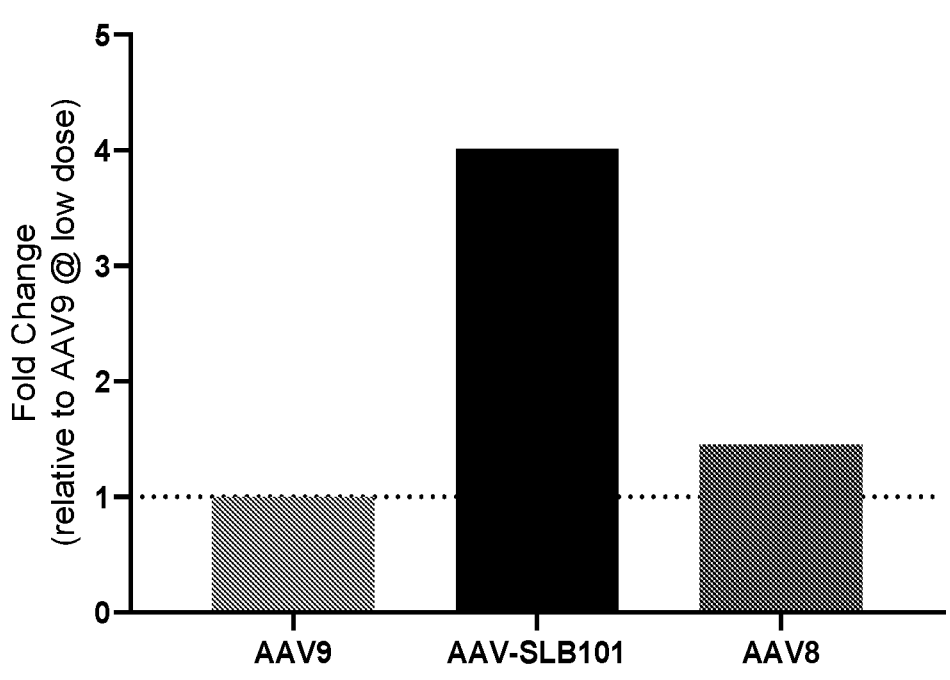

In yet another experiment, patient-derived DMD cells were transduced with the same three AAVs above, but at the lowest MOI only. Cells were harvested 72 hours after transduction, and microdystrophin expression was measured. The data were then normalized to that of AAV9 and plotted in FIG. 1E, and fold change was indicated in the table insert in FIG. 1E. It is apparent that AAV-SLB101 has significantly higher microdystrophin protein expression than AAV9 ($p<0.0001$). Statistics were determined by ordinary one-way ANOVA.

Example 2 In Vitro Potency Assay on C2C12 and DMD Cells

C2C12 cells were transduced at three doses of multiplicity of infection (MOI) with microdystrophin-expressing rAAV vectors packaged in AAV9, AAV8, and the subject capsid AAV-SLB101, respectively. Cells were harvested 72 hours after transduction, and microdystrophin expression was measured. The data shown are mean±SD. Statistical analysis was determined by one-way ANOVA in comparison to AAV9 at each MOI.

Figure 2A:
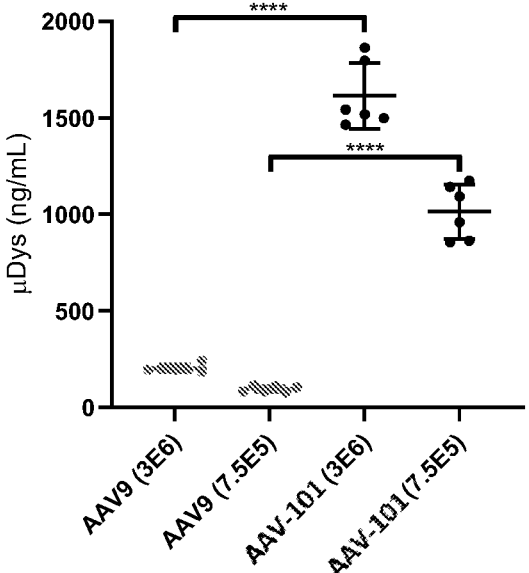
FIGS. 2A and 2B show in vitro potency assay comparing AAV9 and AAV8 with the subject AAV-SLB101 capsid, on both C2C12 cells and patient-derived DMD Mouly cells.
Figure 2A:
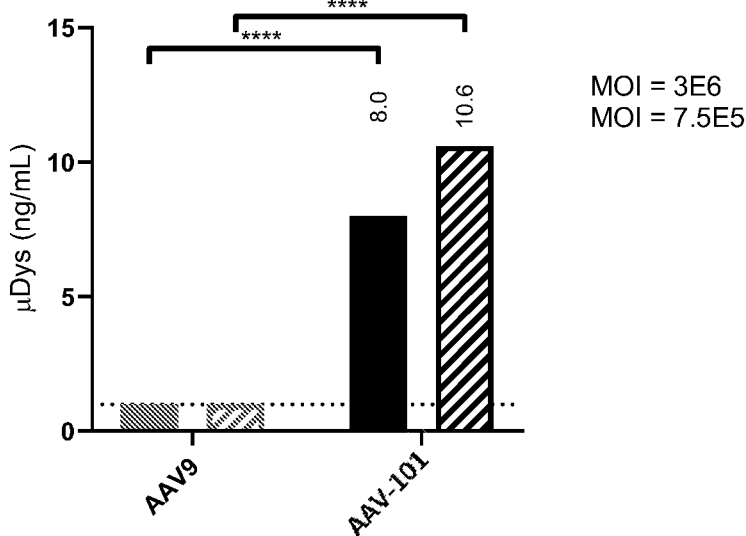

In FIG. 2A, the top panel shows statistically significantly more microdystrophin expression, in two doses (3E6 and 7.5E5), in differentiated C2C12 cells by using rAAV with the subject rAAV capsid, compared to rAAV with AAV9 capsid. In FIG. 2A, the bottom panel shows the same result in bar graph after normalizing to AAV9 at the same MOI. Specifically, at the higher dose of 3E6, expression level was 8.0-fold higher with the subject capsid. At the lower dose of 7.5E5, expression level was 10.6-fold higher with the subject capsid.

Similar experiments were repeated in patient-derived DMD cells—Mouly cells.

Specifically, patient-derived DMD Mouly cells were transduced at three multiplicities of infection (MOIs) with microdystrophin-expressing vectors packaged in AAV9, AAV8, and the subject capsid AAV-SLB101, respectively. Cells were harvested 72 hours after transduction, and microdystrophin expression was measured. The data shown are mean±SD. Statistical analysis was determined by one-way ANOVA in comparison to AAV9 at each MOI.

Figure 2B:
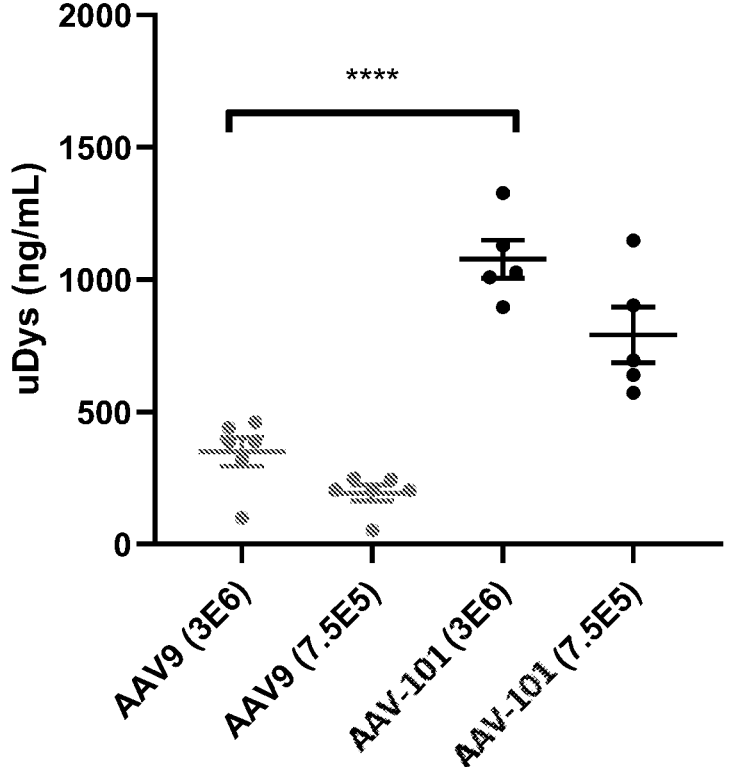
Figure 2B:
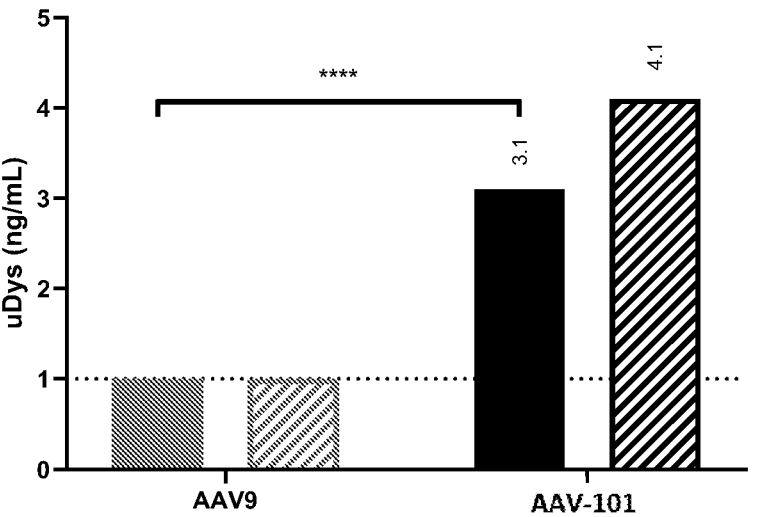

In FIG. 2B, the top panel shows statistically significantly more microdystrophin expression, in two doses (3E6 and 7.5E5), in differentiated DMD Mouly cells by using rAAV with the subject rAAV capsid, compared to rAAV with AAV9 capsid. Outliers were removed from the data. In FIG. 2B, the bottom panel shows the same result in bar graph after normalizing to AAV9 at the same MOI. Specifically, at the higher dose of 3E6, expression level was 3.1-fold higher with the subject capsid. At the lower dose of 7.5E5, expression level was 4.1-fold higher with the subject capsid.

Example 3 In Vivo Comparison of the Subject AAV-SLB101 Capsid to AAV9

The mouse model of DMD—mdx mice—were used in this experiment to demonstrate the superior expression level of microdystrophin in rAAV having the subject capsid, compared to that with AAV9 capsid.

About 5-6 weeks old mdx mice were systemically injected (intravenous delivery) with microdystrophin-expressing rAAV vectors packaged in the subject capsid AAV-SLB101, or in AAV9 capsid, at a dose of 1E14 vg/kg. The mice were necropsied 2-4 weeks post injection (N=3 at 2 weeks, and N=4 at 4 weeks), and tissues were harvested for quantification of vector biodistribution and microdystrophin expression. Statistics in all panels were determined by individual Welch's t tests in comparison to AAV9.

Figure 3A:
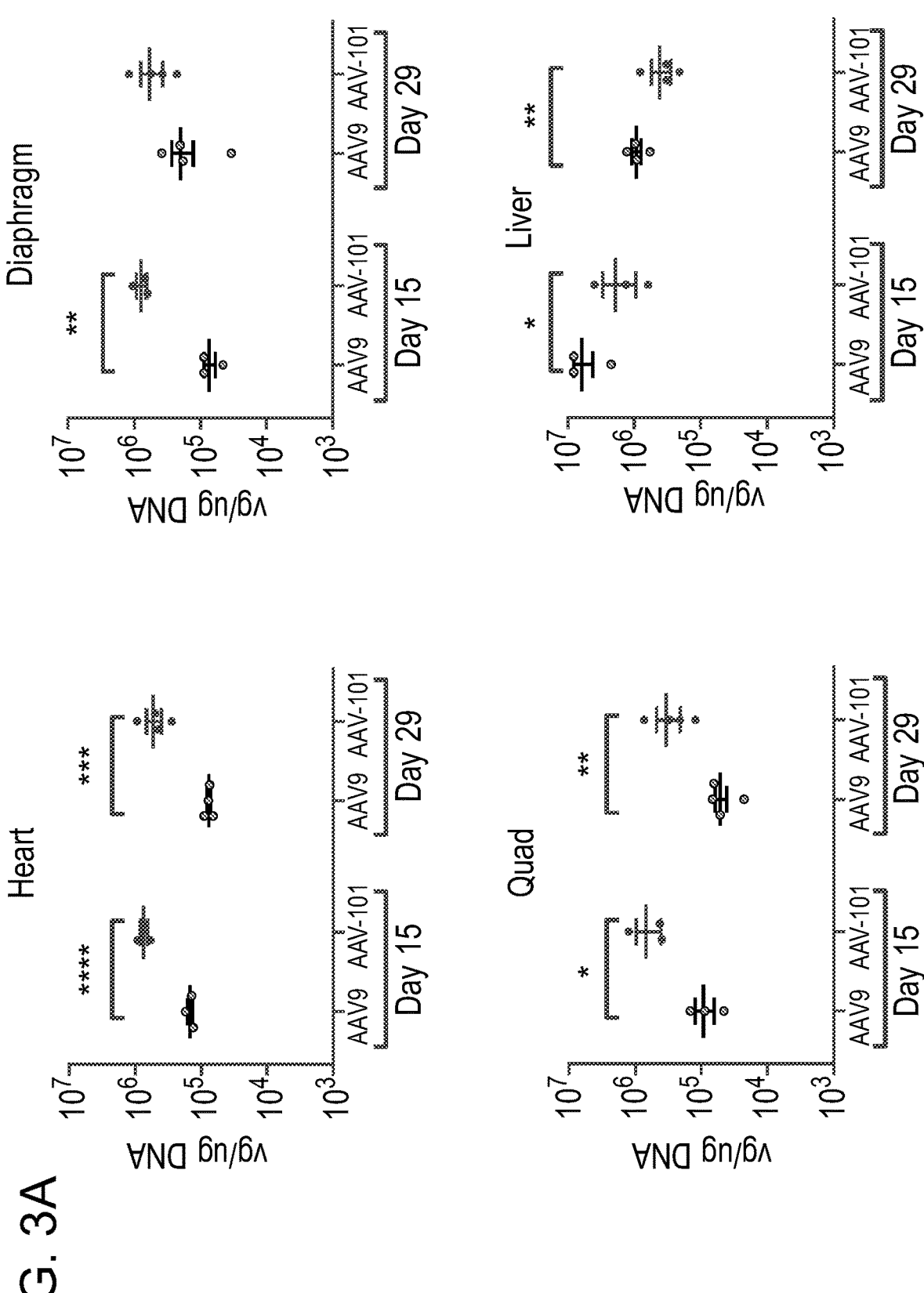
FIGS. 3A-3C show favorable biodistribution and higher level of microdystrophin expression in all three muscle tissues vs. liver tissue, with the subject rAAV capsid as compared to AAV9, and the lack of difference in expression in peripheral tissues such as lung, spleen, kidney, and brain.

FIG. 3A shows that AAV-SLB101 has a significantly higher biodistribution in heart ($p<0.001$) and quadriceps ("quad") ($p<0.01$) in one or both time points (i.e., Day 15 and Day 29), and is trending towards higher vg in diaphragm (particularly at Day 15). Meanwhile, AAV-SLB101 has significantly lower vg in liver than AAV9 ($p<0.01$). The data shown are mean±SD. Statistical analysis was determined by one-way ANOVA in comparison to AAV9 at each time point. No significant difference was found in the brain (data not shown).

Figure 3B:
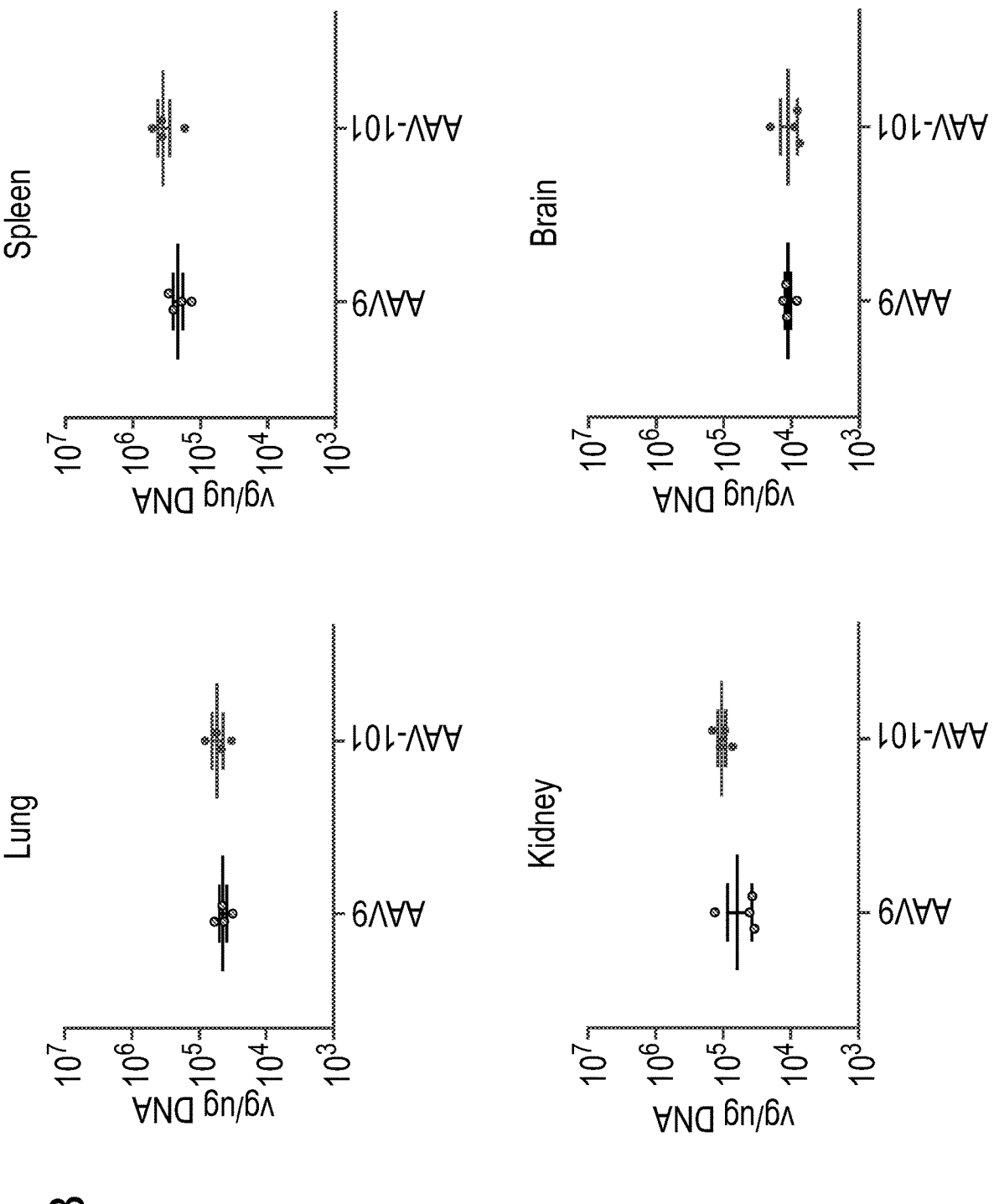

FIG. 3B shows that there is no observable difference in expression in multiple peripheral tissues at Day 29, between rAAV in the subject capsid and rAAV in AAV9 capsid, as expected due to the use of a muscle-specific promoter. The tested peripheral tissues include lung, spleen, kidney, and brain.

Figure 3C:
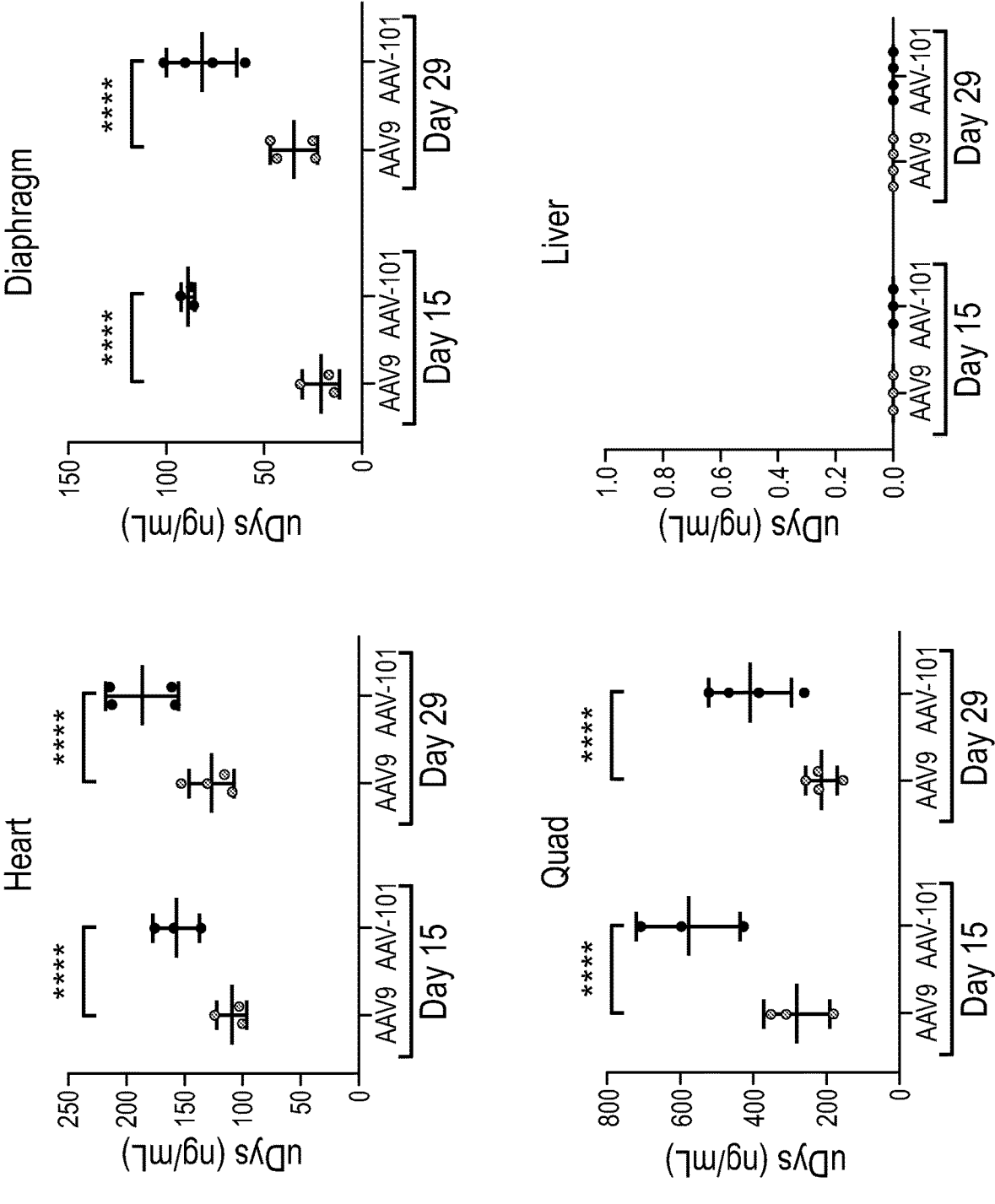

FIG. 3C shows that microdystrophin expression is significantly higher with rAAV packaged in the subject AAV-SLB101 capsid than rAAV packaged in AAV9 capsid, in all three muscle tissues assayed (i.e., heart (cardiac muscle) ($p<0.05$), diaphragm (smooth muscle), and quad (skeletal muscle)) ($p<0.05$), at both Day 15 and Day 29. There is no discernible expression in liver for both constructs. The data shown are mean±SD. Statistical analysis was determined by one-way ANOVA in comparison to AAV9 at each time point.

The above data demonstrates that the subject AAV-SLB101 capsid has superior GOI (e.g., microdystrophin) expression efficiency, in both cultured C2C12 muscle cells, as well as patient-derived DMD Mouly cells, in in vitro potency assays. The in vitro results were also confirmed by in vivo biodistribution study conducted in the mouse DMD model mdx mice.

Specifically, in vivo biodistribution study in mdx mice shows that the subject AAV-SLB101 capsid has a significantly higher biodistribution over AAV9 in heart and quad in both time points tested (i.e., Day 15 and Day 29), and is trending towards higher vg in diaphragm particularly at Day 15. Further, the subject AAV-SLB101 capsid has significantly lower vg in liver, an unintended target tissue for microdystrophin expression.

In terms of microdystrophin expression, the subject AAV-SLB101 capsid has significantly higher level of expression then AAV9 in all three muscle tissues tested.

Example 4 Characterization of Additional Modified AAV-SLB Capsids

Additional modified AAV9 capsids, including AAV-SLB102 to AAV-SLB112, as well as two modified capsids with similar insertion sequences by different surrounding/flanking sequences (AAV-SLB113 and AAV-SLB-114), were constructed and tested for their potency in comparison to wild-type AAV9 and AAV-SLB101. The insertion sequences of AAV-SLB102 to AAV-SLB112 are SEQ ID NOs: 2-12, respectively. See FIG. 6 for a multi-sequence alignments of the tested constructs in relation to wild-type AAV9 sequence and the AAV-SLB101 sequence.

Figure 4:
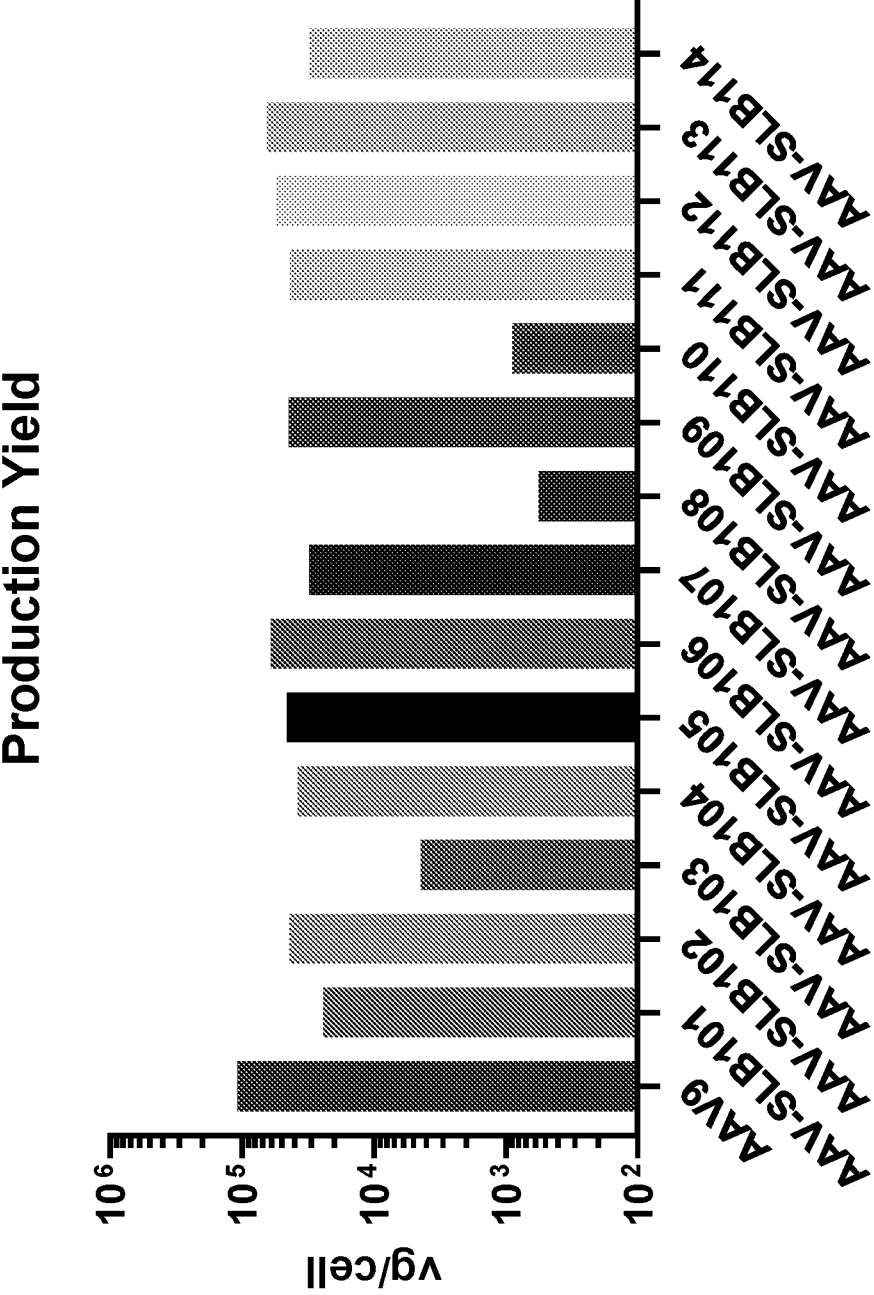
FIG. 4 shows production yield of the novel capsids of the invention compared to wild-type AAV9 capsid. Expanded panel of the subject AAV capsids (AAV-SLB101 to AAV-SLB112) were compared to wild-type AAV9 for AAV yield from triple transfection of adherent 293T cells, and purification via step-wise iodixanol ultracentrifugation. Two additional modified capsids AAV-SLB113 and -SLB114 (see sequence alignments in FIG. 6 below) were also included in the comparison.

In the first experiment, production yield of the various capsid constructs were compared to that of wild-type AAV9 capsid as well as that of AAV-SLB101, based on triple transfection of adherent 293T cells, followed by purification via step-wise iodixanol ultracentrifugation. The measured production yields were plotted in FIG. 4. With a few exceptions, most constructs had similar (but slightly lower) yields compared to wild-type AAV9.

A series of in vitro characterization experiments were performed to compare the additional subject modified AAV9 capsids with wild-type AAV9 and the previously tested AAV-SLB101 in C2C12 cells. The results were reported in FIGS. 5A-5C.

Figure 5A:
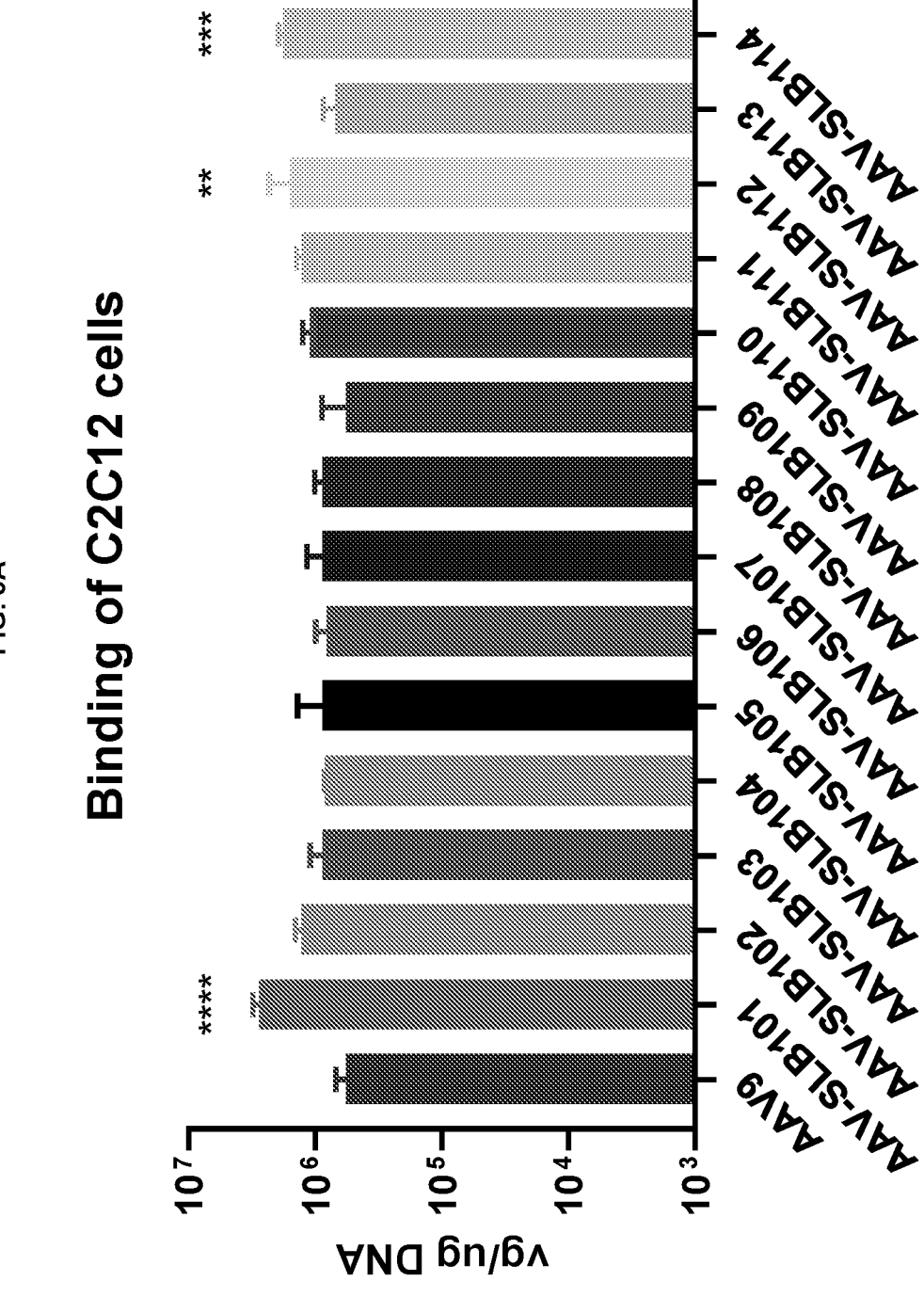
FIGS. 5A-5C show results of in vitro characterization of the subject modified AAV capsids for comparison to wild-type AAV9 capsid in C2C12 Cells. Specifically.

Specifically, quantification of AAV capsid binding to the cell surface of C2C12 cells was measured by qPCR of DNA isolated after 1 hour of incubation at 4° C. The results in FIG. 5A shows that AAV-SLB101 (p<0.0001), 112 (p<0.01) and 114 (p<0.001) all bound to C2C12 cells significantly more than wild-type AAV9, while the remaining constructs all had similar binding compared to wild-type AAV9. Statistics are determined by ordinary one-way ANOVA.

However, there appeared to be a dramatic difference in uptake by C2C12 cells of the somewhat equally bound viral vectors with different modified capsids. Specifically, in FIG. 5B, quantification of uptake of AAV into C2C12 cells was measured by qPCR of DNA isolated after 1 hour of incubation at 4° C. followed by an additional hour at 37° C. The results showed that AAV-SLB101, 102, 108, 111, 112, 113, 114 were taken up by C2C12 cells significantly more (about 20-40 fold more) than AAV9 (p<0.0001). Other tested constructs appeared to have comparable cellular uptake compared to AAV9. Statistics are determined by ordinary one-way ANOVA.

Figure 5B:
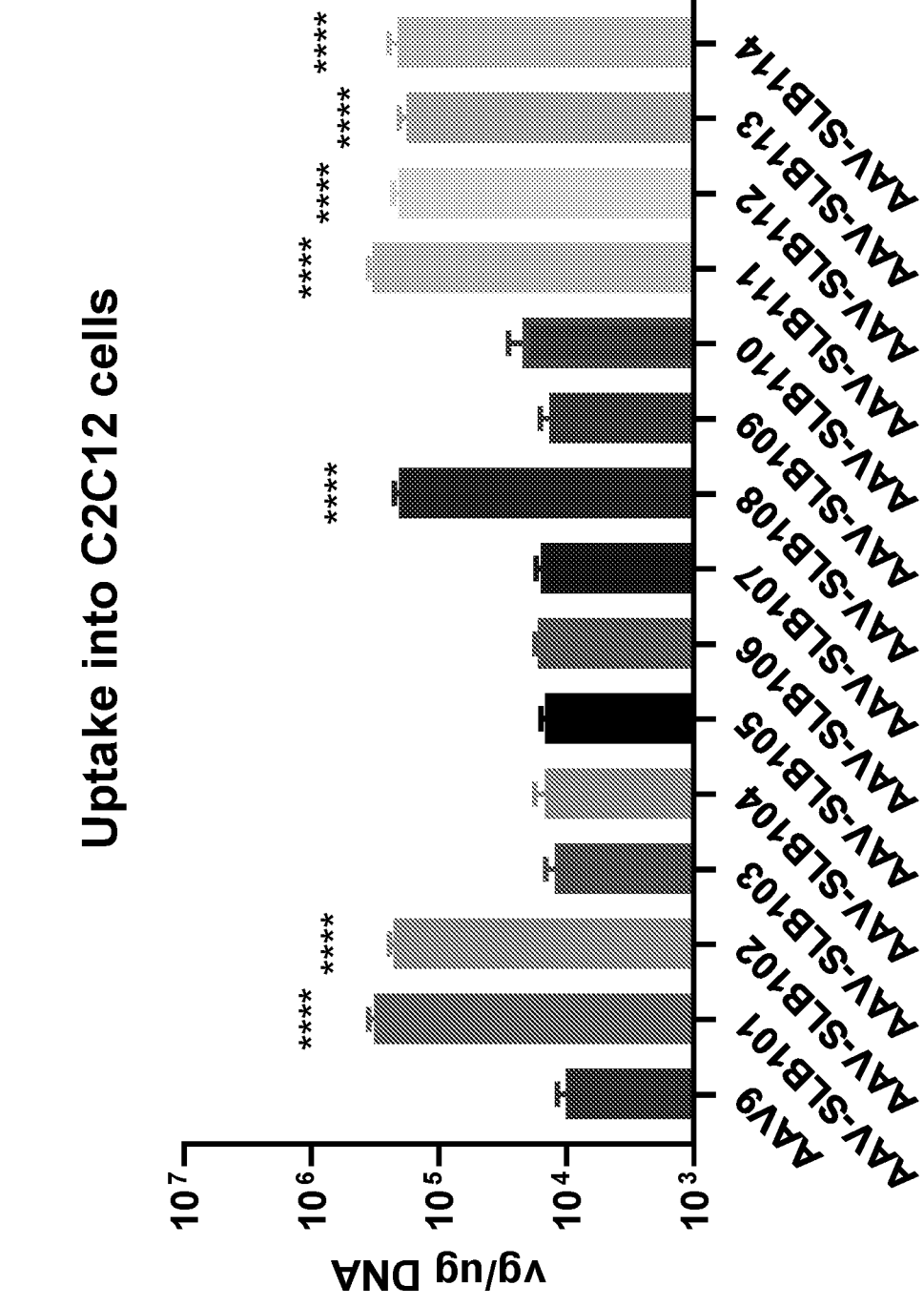
Figure 5C:
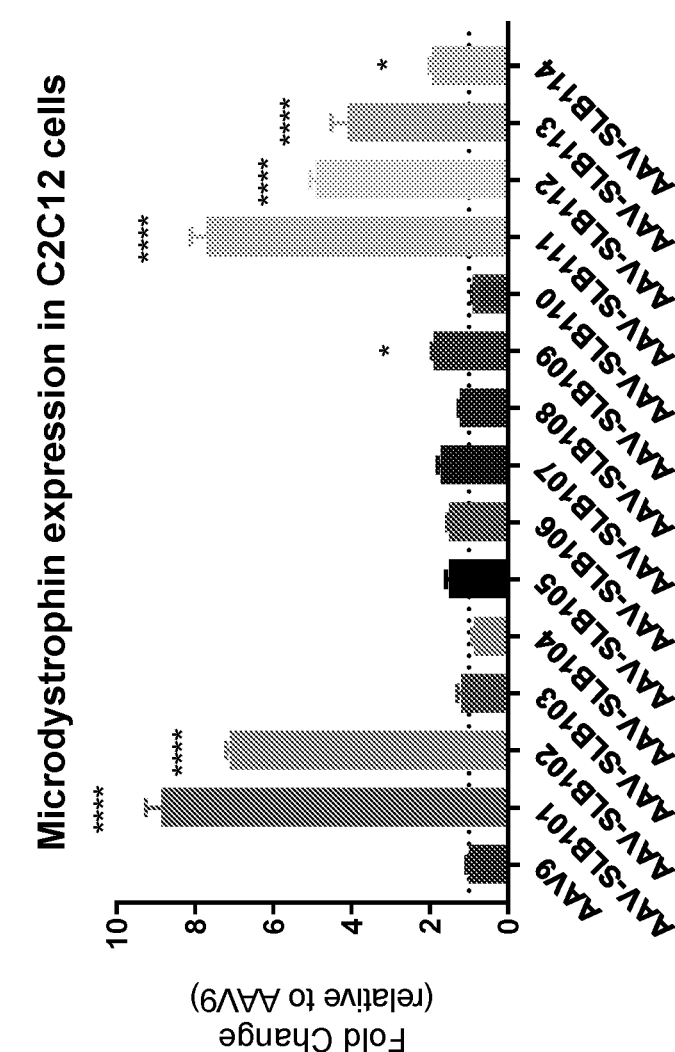

Finally, in FIG. 5C, C2C12 cells were transduced with microdystrophin-expressing vectors packaged in AAV9, AAV-SLB101 and the thirteen additional modified AAV capsids. Cells were harvested 96 hours after transduction, and microdystrophin expression was measured. The data were normalized to that of AAV9, and fold change was indicated in the table insert in FIG. 5C. It is apparent that AAV-SLB101, 102, 111, 112 and 113 had the highest microdystrophin protein expression over AAV9 (p<0.0001), with AAV-SLB109 and 114 resulting in only slightly higher expression than AAV9 (p<0.001). Statistics are determined by ordinary one-way ANOVA.

Notably, despite the fact that SLB101, SLB113, and SLB114 all have the same insertion sequence RGDLGLS, and differ primarily in the flanking sequences, SLB101 appears to lead to much significantly higher microdystrophin-expressing level (8.87:4.11:1.94). That is, SLB101 is 116% more than that of SLB113, which itself is 112% more than that of SLB114.

In summary, the above data shows that at least one of the subject modified AAV9 capsides, AAV-SLB101, showed superior efficiency in comparison to wild-type AAV9 in in vitro assays in both mouse and DMD human skeletal muscle cells. This also translated to increased biodistribution and microdystrophin protein expression in vivo in both quadriceps & heart, and decreased biodistribution to liver, in comparison to AAV9. An expanded panel of the subject modified AAV9 capsids also identified at least two additional candidates interest, AAV-SLB102 and AAV-SLB111, that are similar to AAV-SLB 101 in in vitro assays for binding, uptake, and microdystrophin protein expression in C2C12 cells.

Example 5 Functional Importance of the Sequences Surrounding the Inserted Peptides This example demonstrates the surprising finding that the functions of the modified AAV9 capsids depend on not only the identity of the short peptides inserted into the wild-type AAV9 capsid protein, but also the surrounding sequences of the inserted short peptides.

Functional comparison was made using three representative modified AAV9 capsids—SLB-101, SLB-113, and SLB-114. See sequence alignments in FIG. 6. All three sequences comprise the same 7-residue core sequence RGDLGLS, but differ slightly in the immediate N- and C-terminal sequences surrounding the 7-residue core sequence. In SLB-101, the 7-residue core sequence was inserted between residues 588 and 589 of the wild-type AAV9 VPI sequence (i.e., there is no change of any wild-type AAV9 VPI sequence other than the inserted 7-residue core sequence). See local sequence alignment between wild-type AAV9 and SLB-101 in FIG. 6.

In contrast, in SLB-113 and SLB-114, there are additional changes both within the immediately N-terminal 3-4 residues and within the immediately C-terminal 4-5 residues, with respect to the 7-residue core sequence (see FIG. 6). Overall, the sequences of SLB-113 and SLB-114 appear to be more similar to each other compared to that of SLB-101.

FIG. 5A shows that, in vitro, the ability of these capsids to bind C2C12 cells differs, with SLB-101 and SLB-114 both binding significantly more strongly to C2C12 cells compared to wild-type AAV9, yet SLB-113 showed no significant difference.

In FIG. 5B, C2C12 cells infected by AAV9 variants SLB-101 appeared to express the encoded microdystrophin at a surprisingly higher level than that in SLB-113 and SLB-114.

In order to show that such in vitro results were not due to artifacts associated with the cell line used (i.e., C2C12 cells), in vivo expression studies were designed using the model DMD$^{mdx}$ mice. Specifically, 5-6 weeks old mdx mice were injected with a single dose of 1E14 vg/kg of either wild-type AAV9, or AAV9 with the SLB-101, -102, -113, or -114 variant capsids. SLB-102 was included, although it has a different inserted short peptide (Sec FI. 6). Injected mice were necropsied 2-4 weeks post injection (N=3 @ 2 weeks, and N=3-4 @ 4 weeks). Biodistribution of the virus and microdystrophin expression via MSD were examined in the four groups of mice compared to the wild-type control group.

FIG. 7 shows that SLB-101 and SLB-114 both have significantly increased biodistribution to the quadriceps (skeletal) muscles compared to wild-type AAV9 (6.78-fold and 8.09-fold, respectively). Meanwhile, the modest increases in SLB-102 and -113 are statistically insignificant. Similar observation was also made in the diaphragm (skeletal muscle).

In the heart, SLB-101 biodistribution is significantly higher than that of wild-type AAV9 (4.35-fold). SLB-114 also trended high (2.48-fold) but was not statistically significant. Again, SLB-102 and -113 both had about the same distribution compared to that of the AAV9 control.

Interestingly, although all AAV9 variants had lower liver distribution, only SLB-114 was statistically significantly lower. See FIG. 7.

Extended biodistribution in a number of other organs was also examined. FIG. 8 shows that all had statistically significantly lower distribution in the brain, while distribution in the lung, spleen and kidney appeared to be comparable to that of wild-type AAV9, except that SLB-101 was higher in the kidney, and SLB-114 was higher in the spleen.

Microdystrophin expression was examined in the heart, the quad, and the diaphragm in FIG. 9. Both SLB-101 and SLB-114 had statistically higher expression than wild-type AAV9 in all three tissues, while SLB-102 was unremarkable everywhere. Meanwhile, SLB-113 was only higher in the diaphragm, but was not statistically significantly higher than AAV9 in the two other tissues.

These data showed that at least biodistribution and microdystrophin expression were affected by the surrounding sequences, since SLB-101, -113 and -114 all have the same 7-residue core sequence insertion.

---

The invention claimed is:

1. A modified adeno-associated virus (mAAV) capsid polypeptide consisting of the polypeptide of SEQ ID NO: 14.

2. A modified adeno-associated virus (mAAV) capsid polypeptide comprising the polypeptide of SEQ ID NO: 14.

3. A recombinant adeno-associated virus (rAAV), comprising the mAAV capsid polypeptide of claim 2.

4. The rAAV of claim 3, wherein the rAAV comprises a gene of interest (GOI) flanked by a pair of AAV inverted terminal repeat (ITR) sequences.

5. The rAAV of claim 4, wherein the pair of AAV ITR sequences comprise AAV2 or AAV9 ITR sequences.

6. The rAAV of claim 4, wherein the VP1 capsid of the rAAV consists of or consists essentially of the mAAV capsid polypeptide of claim 2.

7. The rAAV of claim 6, wherein the GOI comprises a gene responsible for/defective in LGMD2E (limb-girdle muscular dystrophy type 2E), LGMD2D (limb-girdle muscular dystrophy type 2D), LGMD2C (limb-girdle muscular dystrophy type 2C), LGMD2B (limb-girdle muscular dystrophy type 2B), LGMD2L (limb-girdle muscular dystrophy type 2L), LGMD2I (limb-girdle muscular dystrophy type 2I), or a gene or coding sequence for a-N-acetylglucosaminidase (NAGLU), sulfamidase (SGSH), Myotubularin 1 (MTM1), Survival of Motor Neuron (SMN), GalNAc transferase (GALGT2), calpain-3 (CAPN-3), acid alpha-glucosidase (GAA), alpha-galactosidase A (GLA), glucocerebrosidase, dystrophin or microdystrophin.

8. The rAAV of claim 6, wherein the GOI encodes a microdystrophin, wherein:

the microdystrophin comprises a coding sequence for R16 and R17 spectrin-like repeats of full-length dystrophin protein; or the microdystrophin comprises a coding sequence for the R1, R16, R17, R23, and R24 spectrin-like repeats of the full-length dystrophin protein.

9. The rAAV of claim 6, wherein the GOI is operatively linked to a transcriptional regulatory cassette.

10. The rAAV of claim 6, wherein the GOI is a microdystrophin gene encoding a protein comprising, from N-to C-terminus, an amino-terminal actin-binding (AB1) domain, a β-dystroglycan binding domain, a Hinge 1 domain (H1), a spectrin-like repeat domain consisting of five spectrin-like repeats that include spectrin-like repeat 1 (SR1), spectrin-like repeat 16 (SR16), spectrin-like repeat 17 (SR17), spectrin-like repeat 23 (SR23), and spectrin-like repeat 24 (SR24), and a Hinge 4 domain (H4), wherein the microdystrophin gene is operatively linked to a muscle-specific human muscle creatine kinase CK8 promoter, and wherein the GOI is flanked by a pair of AAV2 ITR sequences.

11. A polynucleotide encoding the modified adeno-associated virus (mAAV) capsid polypeptide of claim 2.

12. The polynucleotide of claim 11, which is codon-optimized for mammalian expression.

13. A vector comprising the polynucleotide of claim 11.

14. The vector of claim 13, comprising a plasmid or a viral vector.

15. A cultured host cell comprising a recombinant nucleic acid molecule encoding the modified adeno-associated virus (mAAV) capsid polypeptide of claim 2, wherein the recombinant nucleic acid molecule optionally further comprises a heterologous non-AAV sequence.

16. A method of treating muscular dystrophy in a subject in need thereof, the method comprises administering to the subject a therapeutically effective amount of the rAAV of claim 8.

17. The method of claim 16, wherein compared to an otherwise identical reference rAAV with wild-type AAV9 VP1 capsid, the GOI of the rAAV is preferentially expressed in cardiac muscle, skeletal muscle, and/or smooth muscle.

18. The method of claim 16, wherein compared to an otherwise identical reference rAAV with wild-type AAV9 VP1 capsid, the GOI of the rAAV is expressed in liver at a statistically significantly lower level.

19. A method of producing rAAV, wherein the rAAV comprises the mAAV capsid polypeptide of claim 2, the method comprising introducing a rAAV vector encoding a GOI flanked by a pair of ITR sequences to a producing or packaging cell line expressing the mAAV capsid polypeptide of claim 2.

20. The method of claim 19, wherein the producing or packaging cell line is infected by an Herpes Simplex Virus (HSV) vector encoding the mAAV capsid polypeptide of claim 2, or transfected with a sequence encoding the mAAV capsid polypeptide of claim 2.

21. A recombinant adeno-associated virus (rAAV), comprising:

a modified adeno-associated virus (mAAV) capsid polypeptide consisting of the polypeptide of SEQ ID NO: 14, wherein the VP1 capsid of the rAAV consists of or consists essentially of the mAAV capsid polypeptide; and a gene of interest (GOI) flanked by a pair of AAV inverted terminal repeat (ITR) sequences, wherein the GOI is a microdystrophin gene encoding a protein comprising, from N- to C-terminus, an amino-terminal actin-binding (AB1) domain, a ß-dystroglycan binding domain, a Hinge 1 domain (H1), a spectrin-like repeat domain consisting of five spectrin-like repeats that include spectrin-like repeat 1 (SR1), spectrin-like repeat 16 (SR16), spectrin-like repeat 17 (SR17), spectrin-like repeat 23 (SR23), and spectrin-like repeat 24 (SR24), and a Hinge 4 domain (H4), wherein the microdystrophin gene is operatively linked to a muscle-specific human muscle creatine kinase CK8 promoter, and wherein the GOI is flanked by a pair of AAV2 ITR sequences.

* * * * *